US009458482B2

(12) United States Patent
Bals et al.

(10) Patent No.: US 9,458,482 B2
(45) Date of Patent: *Oct. 4, 2016

(54) METHODS OF HYDROLYZING PRETREATED DENSIFIED BIOMASS PARTICULATES AND SYSTEMS RELATED THERETO

(71) Applicants: THE MICHIGAN BIOTECHNOLOGY INSTITUTE, Lansing, MI (US); BOARD OF TRUSTEES OF MICHIGAN STATE UNIVERSITY, East Lansing, MI (US)

(72) Inventors: Bryan Bals, East Lansing, MI (US); Farzaneh Teymouri, Okemos, MI (US); Timothy J. Campbell, East Lansing, MI (US); Bruce E. Dale, Mason, MI (US)

(73) Assignees: THE MICHIGAN BIOTECHNOLOGY INSTITUTE, Lansing, MI (US); BOARD OF TRUSTEES OF MICHIGAN STATE UNIVERSITY, East Lansing, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 14/579,377

(22) Filed: Dec. 22, 2014

(65) Prior Publication Data

US 2015/0112101 A1    Apr. 23, 2015

Related U.S. Application Data

(63) Continuation of application No. 13/458,830, filed on Apr. 27, 2012, now Pat. No. 8,945,245, which is a continuation-in-part of application No. 13/202,011, filed as application No. PCT/US2010/046525 on Aug. 24, 2010, now Pat. No. 8,673,031.

(60) Provisional application No. 61/236,403, filed on Aug. 24, 2009.

(51) Int. Cl.
| | |
|---|---|
| *C10L 5/00* | (2006.01) |
| *C12P 19/14* | (2006.01) |
| *C12P 19/02* | (2006.01) |
| *C12P 7/10* | (2006.01) |
| *C12P 7/14* | (2006.01) |

(52) U.S. Cl.
CPC .................. *C12P 19/14* (2013.01); *C12P 7/10* (2013.01); *C12P 7/14* (2013.01); *C12P 19/02* (2013.01); *C12P 2201/00* (2013.01); *Y02E 50/16* (2013.01); *Y02E 50/30* (2013.01)

(58) Field of Classification Search
CPC ............ C10L 5/44; C12P 19/02; C12P 7/10; C12P 2201/00; C12P 7/14; Y02E 50/16; Y02E 50/30
See application file for complete search history.

(56) References Cited

U.S. PATENT DOCUMENTS

| | | | |
|---|---|---|---|
| 2,017,779 | A | 10/1935 | Vosburgh |
| 2,220,624 | A | 11/1940 | Sherrard et al. |
| 2,548,192 | A | 4/1951 | Berg |
| 3,306,006 | A | 2/1967 | Urban |
| 3,551,549 | A | 12/1970 | Zeeck |
| 3,707,436 | A | 12/1972 | O'Connor |
| 3,920,419 | A | 11/1975 | Schroeder et al. |
| 4,064,276 | A | 12/1977 | Conradsen et al. |
| 4,153,435 | A | 5/1979 | Fischer |
| 4,263,744 | A | 4/1981 | Stoller |
| 4,287,162 | A | 9/1981 | Scheibel |
| 4,356,196 | A | 10/1982 | Hultquist |
| 4,370,351 | A | 1/1983 | Harper |
| 4,461,648 | A | 7/1984 | Foody |
| 4,526,791 | A | 7/1985 | Young |
| 4,581,044 | A | 4/1986 | Uno et al. |
| 4,589,334 | A | 5/1986 | Andersen |
| 4,594,131 | A | 6/1986 | Maier |
| 4,600,590 | A | 7/1986 | Dale |
| 4,642,287 | A | 2/1987 | Inoi et al. |
| 4,848,026 | A | 7/1989 | Dunn-Coleman et al. |
| 4,871,370 | A | 10/1989 | Yatsu et al. |
| 4,986,835 | A | 1/1991 | Uno et al. |
| 4,995,888 | A | 2/1991 | Beaupre et al. |
| 5,025,635 | A | 6/1991 | Rockenfeller et al. |
| 5,037,663 | A | 8/1991 | Dale |
| 5,047,332 | A | 9/1991 | Chahal |
| 5,114,694 | A | 5/1992 | Grotz, Jr. |
| 5,171,592 | A | 12/1992 | Holtzapple et al. |

(Continued)

FOREIGN PATENT DOCUMENTS

| | | |
|---|---|---|
| AU | 756976 B2 | 1/2003 |
| CA | 2368872 A1 | 10/2000 |

(Continued)

OTHER PUBLICATIONS

Kaliyan et al., "Roll Press Briquetting and Pelleting of Corn Stover and Switchgrass", Transactions of the ASABE, American Society of Agricultural and Biological Engineers, vol. 52, No. 2, 2009, pp. 543-555.

(Continued)

*Primary Examiner* — Cephia D Toomer

(57) ABSTRACT

A method is provided in which pretreated and densified cellulosic biomass particulates can be hydrolyzed at a high solids loading rate as compared with the solids loading rate of loose hydrolysable cellulosic biomass fibers. The resulting high concentration sugar-containing stream can be easily converted to biofuels or to an entire suite of other useful bioproducts.

30 Claims, 8 Drawing Sheets

(56) References Cited

U.S. PATENT DOCUMENTS

| | | |
|---|---|---|
| 5,370,999 A | 12/1994 | Stuart |
| 5,660,603 A | 8/1997 | Elliot et al. |
| 5,736,032 A | 4/1998 | Cox et al. |
| 6,027,552 A | 2/2000 | Ruck et al. |
| 6,106,888 A | 8/2000 | Dale et al. |
| 6,176,176 B1 | 1/2001 | Dale et al. |
| 6,255,505 B1 | 7/2001 | Bijl et al. |
| 6,425,939 B1 | 7/2002 | Moreau et al. |
| 6,524,848 B2 | 2/2003 | Mcnelly |
| 6,585,807 B2 | 7/2003 | Umino et al. |
| 6,620,292 B2 | 9/2003 | Wingerson |
| 6,872,296 B2 | 3/2005 | Kim |
| 6,893,484 B2 | 5/2005 | Thomas |
| 7,187,176 B2 | 3/2007 | Lim et al. |
| 7,250,074 B2 | 7/2007 | Tonkovich et al. |
| 7,371,926 B2 | 5/2008 | Sticklen et al. |
| 7,494,675 B2 | 2/2009 | Abbas et al. |
| 7,494,792 B2 | 2/2009 | Warzywoda et al. |
| 7,537,744 B2 | 5/2009 | Benderly et al. |
| 7,585,652 B2 | 9/2009 | Foody et al. |
| 7,771,565 B2 | 8/2010 | Kirov et al. |
| 7,910,338 B2 | 3/2011 | Hennessey et al. |
| 7,910,675 B2 | 3/2011 | Funk et al. |
| 7,915,017 B2 | 3/2011 | Dale |
| 7,937,851 B2 | 5/2011 | Rajagopalan et al. |
| 8,020,342 B2 | 9/2011 | Karpik |
| 8,030,030 B2 | 10/2011 | Varanasi et al. |
| 8,367,378 B2 | 2/2013 | Balan et al. |
| 8,394,177 B2 | 3/2013 | Campbell et al. |
| 8,394,611 B2 | 3/2013 | Dale et al. |
| 8,419,900 B2 | 4/2013 | Baba et al. |
| 8,444,925 B2 | 5/2013 | Baba |
| 8,651,403 B2 | 2/2014 | Camp et al. |
| 8,673,031 B2 | 3/2014 | Dale et al. |
| 8,771,425 B2 | 7/2014 | Dale |
| 8,846,123 B2 | 9/2014 | Zeeck |
| 8,945,245 B2 * | 2/2015 | Bals ............ C12P 19/14 435/72 |
| 8,968,515 B2 | 3/2015 | Balan et al. |
| 8,980,599 B2 | 3/2015 | Tolan et al. |
| 9,039,792 B2 | 5/2015 | Dale |
| 2003/0044951 A1 | 3/2003 | Sporleder et al. |
| 2005/0064577 A1 | 3/2005 | Berzin |
| 2006/0130396 A1 | 6/2006 | Werner |
| 2007/0029252 A1 | 2/2007 | Dunson, Jr. et al. |
| 2007/0031918 A1 | 2/2007 | Dunson, Jr. et al. |
| 2007/0037259 A1 | 2/2007 | Hennessey et al. |
| 2007/0113736 A1 | 5/2007 | Bandosz |
| 2007/0192900 A1 | 8/2007 | Sticklen |
| 2007/0202214 A1 | 8/2007 | Lewis et al. |
| 2007/0287795 A1 | 12/2007 | Huda et al. |
| 2008/0008783 A1 | 1/2008 | Dale |
| 2008/0057555 A1 | 3/2008 | Nguyen |
| 2008/0087165 A1 | 4/2008 | Wright et al. |
| 2008/0115415 A1 | 5/2008 | Agrawal et al. |
| 2008/0171297 A1 | 7/2008 | Reynolds et al. |
| 2008/0229657 A1 | 9/2008 | Senyk et al. |
| 2008/0256851 A1 | 10/2008 | Lumb |
| 2008/0264254 A1 | 10/2008 | Song et al. |
| 2008/0280236 A1 | 11/2008 | Wright |
| 2009/0011474 A1 | 1/2009 | Balan et al. |
| 2009/0042259 A1 | 2/2009 | Dale et al. |
| 2009/0049748 A1 | 2/2009 | Day et al. |
| 2009/0053770 A1 | 2/2009 | Hennessey et al. |
| 2009/0053771 A1 | 2/2009 | Dale et al. |
| 2009/0064569 A1 | 3/2009 | Khater |
| 2009/0087898 A1 | 4/2009 | Haase et al. |
| 2009/0093027 A1 | 4/2009 | Balan et al. |
| 2009/0099079 A1 | 4/2009 | Emalfarb et al. |
| 2009/0123361 A1 | 5/2009 | Johannessen et al. |
| 2009/0178671 A1 | 7/2009 | Ahring et al. |
| 2009/0230040 A1 | 9/2009 | Limcaco |
| 2009/0313976 A1 | 12/2009 | Johannessen et al. |
| 2009/0318670 A1 | 12/2009 | Dale et al. |
| 2010/0159521 A1 | 6/2010 | Cirakovic et al. |
| 2010/0267999 A1 | 10/2010 | Lau et al. |
| 2010/0279361 A1 | 11/2010 | South et al. |
| 2011/0192559 A1 | 8/2011 | Venkatesh et al. |
| 2011/0201091 A1 | 8/2011 | Dale |
| 2011/0290114 A1 | 12/2011 | Campbell et al. |
| 2011/0300269 A1 | 12/2011 | Dale et al. |
| 2012/0064574 A1 | 3/2012 | Tokuyasu et al. |
| 2012/0071308 A1 | 3/2012 | Sekar |
| 2012/0085505 A1 | 4/2012 | Sabourin |
| 2012/0125548 A1 | 5/2012 | Cohen |
| 2012/0125551 A1 | 5/2012 | Cohen et al. |
| 2012/0187228 A1 | 7/2012 | Camp et al. |
| 2012/0325202 A1 | 12/2012 | Dale |
| 2013/0196398 A1 | 8/2013 | Bals et al. |
| 2013/0217073 A1 | 8/2013 | Chundawat et al. |
| 2013/0244293 A1 | 9/2013 | Balan et al. |
| 2013/0247456 A1 | 9/2013 | Dale et al. |
| 2013/0280762 A1 | 10/2013 | Dale et al. |
| 2013/0289268 A1 | 10/2013 | Teymouri et al. |
| 2014/0038243 A1 | 2/2014 | Balan et al. |
| 2014/0227757 A1 | 8/2014 | Jin et al. |
| 2015/0125907 A1 | 5/2015 | Balan et al. |

FOREIGN PATENT DOCUMENTS

| | | |
|---|---|---|
| CA | 2573046 A1 | 1/2006 |
| CA | 2610797 A1 | 12/2006 |
| CA | 2752604 A1 | 8/2010 |
| CA | 2797193 A1 | 10/2011 |
| CA | 2762985 C | 7/2013 |
| CA | 2650860 C | 9/2013 |
| CA | 2737704 C | 11/2013 |
| CA | 2760840 C | 12/2015 |
| CN | 102597247 A | 7/2012 |
| CN | 102939388 A | 2/2013 |
| DE | 20301645 U1 | 4/2003 |
| EP | 0077287 A2 | 4/1983 |
| EP | 0144930 A2 | 6/1985 |
| EP | 1247781 A2 | 10/2002 |
| EP | 1533279 A1 | 5/2005 |
| EP | 2411492 A2 | 2/2012 |
| EP | 2561084 A2 | 2/2013 |
| EP | 2841588 A2 | 3/2013 |
| GB | 1310835 A | 3/1973 |
| GB | 1381728 A | 1/1975 |
| GB | 2122864 A | 1/1984 |
| IN | 249187 A1 | 10/2011 |
| IN | 9645/DELNP/2011 A | 2/2013 |
| JP | 2008-161125 A | 7/2006 |
| JP | 2008-535664 A | 9/2008 |
| JP | 2011-160753 A | 8/2011 |
| RU | 2215755 C1 | 11/2003 |
| WO | 85/00133 A1 | 1/1985 |
| WO | 00/61858 A1 | 10/2000 |
| WO | 01/32715 A1 | 5/2001 |
| WO | 02/37981 A2 | 5/2002 |
| WO | 03/114139 A3 | 12/2003 |
| WO | 2004/033920 A1 | 4/2004 |
| WO | 2005091418 A2 | 9/2005 |
| WO | 2006/055362 A1 | 5/2006 |
| WO | 2006/128304 A1 | 12/2006 |
| WO | 2007/005918 A2 | 1/2007 |
| WO | 2007/130337 A1 | 11/2007 |
| WO | 2008/020901 A2 | 2/2008 |
| WO | 2008/114139 A2 | 9/2008 |
| WO | 2009/011474 A1 | 1/2009 |
| WO | 2009/025547 A1 | 2/2009 |
| WO | 2009/058276 A1 | 5/2009 |
| WO | 2010/098408 A1 | 9/2010 |
| WO | 2010/121348 A1 | 10/2010 |
| WO | 2010/035679 A1 | 11/2010 |
| WO | 2010/135679 A1 | 11/2010 |
| WO | 2010/147218 A1 | 12/2010 |
| WO | 2011/028543 A1 | 3/2011 |
| WO | 2011/046818 A2 | 4/2011 |
| WO | 2011/028543 A3 | 6/2011 |
| WO | 2011/080154 A1 | 7/2011 |
| WO | 2011/125056 A1 | 10/2011 |
| WO | 2011/133571 A2 | 10/2011 |

(56) References Cited

FOREIGN PATENT DOCUMENTS

| WO | 2011/133571 A3 | 1/2012 |
|---|---|---|
| WO | 2012/012594 A1 | 1/2012 |
| WO | 2012/071312 A2 | 5/2012 |
| WO | 2012/088429 A2 | 6/2012 |
| WO | 2013/106113 A2 | 7/2013 |
| WO | 2013/131015 A1 | 9/2013 |
| WO | 2013/106113 A3 | 10/2013 |
| WO | 2013/163571 A2 | 10/2013 |
| WO | 2013/163571 A3 | 3/2014 |

OTHER PUBLICATIONS

Kawasaki et al., "Deodorization of Ammonia by Coffee Grounds", Journal of Oleo Science, vol. 55, No. 1, 2006, pp. 31-35.

Kim et al., "Lime Pretreatment and Enzymatic Hydrolysis of Corn Stover", Bioresource Technology, vol. 96, No. 18, Mar. 2005, pp. 1994-2006.

Kim et al., "Pretreatment and Fractionation of Corn Stover by Ammonia Recycle Percolation Process", Bioresource Technology, vol. 96, No. 18, 2005, pp. 2007-2013.

Kim et al., "Pretreatment of Corn Stover by Low-Liquid Ammonia Recycle Percolation Process", Applied Biochemistry and Biotechnology, vol. 133, Apr. 2006, pp. 41-57.

Klemm et al., "General Considerations on Structure and Reactivity of Cellulose", Chapter 2.1-2.1.4, Comprehensive Cellulose Chemistry: Fundamentals and Analytical Methods, vol. 1, 2004, pp. 9-29.

Kumar et al., "Does Densification Influence the Steam Pretreatment and Enzymatic Hydrolysis of Softwoods to Sugars?", Bioresource Technology, vol. 121, Oct. 2012, 38 pages.

Kumar et al., "Methods for Pretreatment of Lignocellulosic Biomass for Efficient Hydrolysis and Biofuel Production", Industrial and Engineering Chemistry Research, vol. 48, No. 8, 2009, 18 pages.

Lau et al., "Cellulosic Ethanol Production from APEX-treated Corn Stover Using *Saccharomyces cerevisiae* 424A (LNH-ST)", PNAS, vol. 106, No. 5, Feb. 3, 2009, pp. 1368-1373.

Lau et al., "Comparing the Fermentation Performance of *Escherichia coli* KO11, *Saccharomyces cerevisiae* 424A (LNH-ST) and *Zymornanas mobilis* AX101 for Cellulosic Ethanol Production", Biotechnology for Biofuels, vol. 3, No. 11, 2010, 10 pages.

Lau et al., "Ethanol Fermentation of *E. coli* KO11 in Hydrolysate from AFEX-treated Corn Stover", Biomass Conversion Research Laboratory, Department of Chemical Engineering and Materials Science, Michigan State University, Apr. 30, 2006, 1 page.

Lau et al., "The Impacts of Pretreatment on the Fermentability of Pretreated Lignocellulosic Biomass: A Comparative Evaluation between Ammonia Fiber Expansion and Dilute Acid Pretreatment", Biotechnology for Biofuels, vol. 2, No. 30, 2009, 11 pages.

Laureano-Perez et al., "Understanding Factors That Limit Enzymatic Hydrolysis of Biomass: Characterization of Pretreated Pretreated Corn Stover", Applied Biochemistry and Biotechnology, vol. 121-124, 2005. pp. 1081-1099.

Lewin et al., "The Effect of Liquid Anhydrous Ammonia in the Structure and Morphology of Cotton Cellulose", Journal of Polymer Science Part C: Polymer Symposia, vol. 36, No. 1, 1971, pp. 213-229.

Liu et al., "Partial Flow of Compressed-Hot Water through Corn Stover to Enhance Hemicellulose Sugar Recovery and Enzymatic Digestibility of Cellulose", Bioresource Technology, vol. 96, No. 18, 2005, pp. 1978-1985.

Mani et al., "Grinding Performace and Physical Properties of Wheat and Barley Straws, Corn Stover, and Switchgrass", Biomass and Bioenergy, vol. 27, 2004, pp. 339-352.

Marshall et al., "Complete Rations for Dairy Cattle. II. Sugarcane Bagasse Pellets as Roughage in Blended Rations for Lactating Cows", Journal of Dairy Science, vol. 58, No. 6, Jun. 1975, pp. 896-900.

Mellerowicz et al., "Unravelling Cell Wall Formation in the Woody Dicot Stern", Plant Molecular Biology, vol. 47, 2001, pp. 239-274.

Miller, Norman G., "Phase I Biomass Enhanced Refined Lignite Demonstration Project", Project, Dec. 15, 2008, 24 pages.

Mohan et al., "Pyrolysis of Wood/Biomass for Bio-oil: A Critical Review", Energy and Fuels, vol. 20, No. 3, 2006, pp. 846-889.

Mosler et al., "Features of Promising Technologies for Pretreatment of Lignocellulosio Biomass", Bioresource Technology, vol. 96, 2005, pp. 673-686.

Mosier et al., "Optimization of pH Controlled Liquid Hot Water Pretreatment of Corn Stover", Bioresource Technology, vol. 96, 2005, pp. 1986-1993.

Nenkova et al., "Production of Phenol Compounds by Alkaline Treatment of Technical Hydrolysis Lignin and Wood Biomass", Chemistry of Natural Compounds, vol. 44, No, 2, 2008, pp. 182-185.

Nwodo at al., "Xylanase Production of *Aspergillus niger* and *Penicillium chrysogenum* from Ammonia Pretreated Cellulosic Waste", Research Journal of Microbiology, vol. 3, No. 4, 2008, pp. 246-253.

Owen et al., "An infrared Study of the Effect of Liquid Ammonia on Wood Surfaces", Journal of Molecular Structure, vol. 198, Jul. 1989, pp. 435-449.

Perez et al., "TEMPO-Mediated Oxidation of Cellulose III", Biomacromolecules, vol. 4, No. 5, 2003, pp. 1417-1425.

Perry et al., "Reaction Kinetics and Reactor Design", Chemical Engineers' Handbook, Fourth Edition, 1963, pp. 4-21-4-24.

Piva et al., "Detoxification Methods of Aflatoxins. A Review", Nutrition Research, vol. 15, No. 5, May 1995, pp. 767-776.

Prévot-D'Alvise et al., "Development of a Pilot Process for the Production of Alfalfa Peptide isolate", Journal of Chemical Technology and Biotechnology, vol. 78, No. 5, May 2003, pp. 518-528.

Rijal et al., "Combined Effect of Pelleting and Pretreatment on Enzymatic Hydrolysis of Switchgrass", Bioresource Technology, vol. 116, 2012, pp. 36-41.

Rollin et al., "Increasing Cellulose Accessibility is More Important Than Removing Lignin: A Comparison of Cellulose Solvent-Based Lignocellulose Fractionation and Soaking in Aqueous Ammonia", Biotechnology and Bioengineering, vol. 108, No. 1, Jan. 1, 2011, pp. 22-30.

Roman-Ponce et al., "Complete Rations for Dairy Cattle. V. Interaction of Sugarcane Bagasse Quantity and Form with Soybean Meal, Urea, and Starea", Journal of Dairy Science, vol. 58, No. 9, Sep. 1975, pp. 1320-1327.

Selig et al., "Enzymatic Saccharification of Lignocellulosic Biomass", National Renewable Energy Laboratory, Technical Report, NREL/TP-510-42629, Mar. 21, 2008, 8 pages.

Sendich et al., "Recent Process Improvements for the Ammonia Fiber Expansion (AFEX) Process and Resulting Reductions in Minimum Ethanol Selling Price", Bioresource Technology, vol. 99, 2008, pp. 8429-8435.

Sheridan et al., "Assessment of the Influence of Media Particle Size on the Biofiltration of Odorous Exhaust Ventilation Air From a Piggery Facility", Bioresource Technology, vol. 84, 2002, pp. 129-143.

Singhania et al., "Advancement and Comparative Profiles in the Production Technologies Using Solid-State and Submerged Fermentation for Microbial Cellulases", Enzyme and Microbial Technology, vol. 46, 2010, pp. 541-549.

Sokhansanj et al., "Biomass Densification—Cubing Operation and Costs for Corn Stover", Applied Engineering in Agriculture, vol. 20, No. 4, 2004, pp. 495-499.

Somerville et al., "Toward a Systems Approach to Understanding Plant Cell Walls", Science, vol. 306, No. 5705, Dec. 2004, pp. 2206-2211.

Sun et al., "Hydrolysis of Lignocellulosic Materials for Ethanol Production: A Review", Bioresource Technology, vol. 83, No. 1, May 2002, pp. 1-11.

Tabil et al., "Biomass Feedstock Pre-Processing—Part 1: Pre-Treatment", Chapter 18, Biofuel's Engineering Process Technology, Aug. 2011, pp. 411-438.

Tanner Industries, Inc., "Anhydrous Ammonia", Customer Manual, Dec. 2006, 17 pages.

(56) References Cited

OTHER PUBLICATIONS

Teymouri et al., "Optimization of the Ammonia Fiber Explosion (AFEX) Treatment Parameters for Enzymatic Hydrolysis of Corn Stover", Bioresource Technology, vol. 96, 2005, pp. 2014-2018.
Theerarattananoon et al., "Effects of the Pelleting Conditions on Chemical Composition and Sugar Yield of Corn Stover, Big Bluestein, Wheat Straw, and Sorghum Stalk Pellets", Bioprocess and Biosystems Engineering, vol. 35, No. 4, May 2012, pp. 615-623.
Van Horn et al., "Complete Rations for Growing Dairy Replacements Utilizing By-Product Feedstuff", Journal of Dairy Science, vol. 63, Dairy Science Department, University of Florida, Gainesville, 1980, pp. 1465-1474.
Wada et al., "Neutron Crystallographic and Molecular Dynamics Studies of the Structure of Ammonia-Cellulose I: Rearrangement of Hydrogen Bonding during the Treatment of Cellulose with Ammonia", Cellulose, vol. 18, No. 2, Apr. 2011, pp. 191-206.
Wada et al., "Polymorphism of Cellulose I Family: Reinvestigation of Cellulose IVI", Biomacromolecules, vol. 5, No. 4 (Abstract), 2004, pp. 1385-1391.
Waiss et al., "Improving Digestibility of Straws for Ruminant Feed by Aqueous Ammonia", Journal of Animal Science, vol. 35, No. 1, 1972, pp. 109-112.
Walter. A., "Industrial Uses of Biomass Energy: New Technologies for Modern Biomass Energy Carriers", Taylor and Francis, Chapter 9, Edited by Rosillo-Calle F., Bajay S.V., Rothman H., 2000, pp. 200-253.
Wang et al., "Cost Estimates and Sensitivity Analyses for the Ammonia Fiber Explosion Process", Applied Biochemistry and Biotechnology, vol. 70-72, No. 1, 1998, pp. 51-66.
Wilson, Jonathan, "A Cost Analysis for the Densification and Transportation of Cellulosic Biomass for Ethanol Production", A Thesis, 2011, 86 pages.
Office Action received for Canadian Patent Application No. 2,760,840, mailed on Mar. 28, 2012, 3 pages.
Office Action received for Canadian Patent Application No. 2,760,840, mailed on Aug. 6, 2012, 4 pages.
Office Action received for Canadian Patent Application No. 2,760,840, mailed on Jan. 3, 2013, 3 pages.
Office Action received for Canadian Patent Application No. 2,760,840, mailed on Jul. 30, 2013, 4 pages.
Office Action received for Canadian Patent Application No. 2,762,985 mailed on Mar. 13, 2012, 4 pages.
Office Action received for Canadian Patent Application No. 2,822,644, mailed on Sep. 8, 2014, 2 pages.
Patent Examination Report received for Australian Patent Application No. 2010289797, issued on Oct. 30, 2012, 4 pages.
Office Action received for Chinese Patent Application No. 201110097994.X, mailed on Mar. 27, 2013, 7 pages of English Translation.
Patent Examination Report received for Australian Patent Application No. 2011201768, issued on Jun. 21, 2012, 3 pages.
Patent Examination Report received for Australian Patent Application No. 2013205681, issued on Jun. 27, 2013, 4 pages.
Patent Examination Report received for Australian Patent Application No. 2011348161, issued on Feb. 21, 2014, 4 pages.
Office Action received for Chinese Patent Application No. 201180062555.3, mailed on Oct. 14, 2014, 9 pages of English translation and 8 pages of Official Notice.
Office Action received for Chinese Patent Application No. 201210287568.7, dated on Jul. 12, 2013, 2 pages of English Translation and 5 pages of official copy.
Office Action received for Chinese Patent Application No. 201210287568.7, mailed on Nov. 4, 2014, 3 pages of English translation and 3 pages of Official Notice.
International Search Report and Written Opinion received for PCT Application No. PCT/US2010/046525, mailed on Apr. 29, 2011, 9 pages.
International Preliminary Report on Patentability received for PCT Patent Application No. PCT/US2010/046525, issued on Feb. 28, 2012, 5 pages.
International Search Report and Written Opinion received for PCT Patent Application No. PCT/US2007/010415, mailed on Oct. 11, 2007, 5 pages.
International Search Report and Written Opinion for PCT Patent Application No. PCT/US2011/038524, mailed on Feb. 9, 2012, 7 pages.
International Search Report and Written Opinion received for PCT Patent Application No. PCT/US2011/061617, mailed on Jun. 8, 2012, 10 pages.
International Preliminary Report on Patentability received for PCT Application No. PCT/US2011/066868, mailed on Jul. 4, 2013, 5 pages.
International Search Report and Written Opinion received for PCT Patent Application No. PCT/US2011/066868, mailed on Sep. 19, 2012, 6 pages.
International Search Report and Written Opinion received for PCT Application No. PCT/US2012/059898, mailed on Jul. 26, 2013, 11 pages.
International Search Report and Written Opinion received for PCT Patent Application No. PCT/US2013/028689, mailed on Jun. 4, 2013, 5 pages.
International Search Report received for PCT Patent Application No. PCT/US2013/037935, mailed on Jul. 19, 2013, 4 pages.
Adapa et al., "Compression Characteristics of Selected Ground Agricultural Biomass", Agricultural Engineering International: The CIGR Ejournal, vol. 11, Manuscript 1347, Jun. 2009, 19 pages.
Adapa et al., "Pelleting Characteristics of Selected Biomass With and Without Steam Explosion Pretreatment", Int. J. Agric. and Biol Eng, vol. 3, No. 3, Sep. 2010, pp. 62-79.
Alizadeh et al., "Pretreatment of Switchgrass by Ammonia Fiber Explosion (AFEX)", Applied Biochemistry and Biotechnology, vol. 121-124, 2005, pp. 1133-1141.
Bagga et al., "Evidence for the Occurrence of Polyamine Oxidase in the Dicotyledonous Plant *Medicago sativa* L. (alfalfa)", Plant Cell Reports, vol. 10, No. 11, 1991, pp. 550-554.
Balan et al., "Lignocellulosic Biomass Pretreatment Using AFEX", Biofuels: Methods and Protocols, Methods in Molecular Biology, Chapter 5, vol. 581, 2009, pp, 61-77.
Bals et al., "Evaluating the Impact of Ammonia Fiber Expansion (AFEX) Pretreatment Conditions on the Cost of Ethanol Production", Bioresource Technology, vol. 102, 2011, pp. 1277-1283.
Bergner et al., "Archives of Animal Nutrition", Arch. Tierernahr, vol. 30, 1980, pp. 239-256.
Campbell et al., "A Packed Bed Ammonia Fiber Expansion Reactor System for Pretreatment of Agricultural Residues at Regional Depots", Biofuels, vol. 4, No. 1, 2013, pp. 23-34.
Carolan et al., "Technical and Financial Feasibiiity Analysis of Distributed Bioprocessing Using Regional Biomass Pre-Processing Centers", Journal of Agricultural and Food Industrial Organization, vol. 5, No. 2, Article 10, 2007, 29 pages.
Chahal, D.S., "Bioconversion of Hemicelluloses into Useful Products in an Integrated Process for Food/Feed and Fuel (Ethanol) Production from Biomass", Biotechnology and Bioengineering Symposium, No. 14, 1984, pp. 425-433.
Chang, Shu-Ting, "The World Mushroom Industry: Trends and Technological Development", International Journal of Medicinal Mushrooms, vol. 8, 2006, pp. 297-314.
Chundawat et al., "Effect of Particle Size Based Separation of Milled Corn Stover on AFEX Pretreatment and Enzymatic Digestibility", Biotechnology and Bioengineering, vol. 96, No. 2, Feb. 1, 2007, pp. 219-231.
Chundawat et al., "Multi-scale Visualization and Characterization of Lignocellulosic Plant Cell Wall Deconstruction During Thermochemical Pretreatment", Energy Environmental Science, 2011, vol. 4, 2011, pp. 973-984.
Cosgrove, Daniel J., "Growth of the Plant Cell Wall", Nature Reviews Molecular Cell Biology, vol. 6, Nov. 2005, pp. 850-861.
Dale et al., "Extrusion Processing for Ammonia Fiber Explosion (AFEX)", Applied Biochemistry and Biotechnology, vol. 77-79, 1999, pp. 35-45.

(56) References Cited

OTHER PUBLICATIONS

Deshusses, Marc A., "Biological Waste Air Treatment in Biofilters", Current Opinion in Biotechnology, vol. 8, 1997, pp. 335-339.
Eggeman, T., "Boundary Analysis for $H_2$ Production by Fermentation", Subcontract Report NREL/SR-560-36129, May 2002, 17 pages.
Erickson, David R., "Edible Fats and Oils Processing: Basic Principles and Modern Practices", World Conference Proceedings, AOCS Press, 1990, 6 pages.
Eriksson et al., "A Model Explaining Declining Rate in Hydrolysis of Lignocellulose Substrates with Cellobiohydrolase I (Cel7A) and Endoglucanase I (Cel7B) of *Trichoderma reesei*", Applied Biochemistry and Biotechnology, vol. 101, No. 1, Apr. 2002, pp. 41-60.
Ferrer et al., "NR 06. Sugar Production from Rice Straw", Arch. Latinoam. Prod. Anim., vol. 5, No. 1, 1997, pp. 112-114.
Gao et al., "Mixture Optimization of Six Core Glycosyl Hydrolases for Maximizing Saccharification of Ammonia Fiber Expansion (AFEX) Pretreated Corn Stover", Bioresource Technology, vol. 101, No. 8, Apr. 2010, pp. 2770-2781.
Habibi et al., "Optimization of Cellouronic Acid Synthesis by TEMPO-Mediated Oxidation of Cellulose III from Sugar Beet Pulp", Cellulose, vol. 15, No. 1 (Abstract), Feb. 2008, pp. 177-185.
Igarashi et al., "Activation of Crystalline Cellulose-to-Cellulose III, Results in Efficient Hydrolysis by Cellobiohydrolase", FEBS Journal, vol. 274, No. 7, Apr. 2007, pp. 1785-1792.
Ishikawa et al., "Determination of Parameters in Mechanical Model for Cellulose III Fibre", Polymer, vol. 39, No. 10, May 1998, pp. 1875-1878.
Jin et al., "A Novel Integrated Biological Process for Cellulosic Ethanol Production Featuring High Ethanol Productivity, Enzyme Recycling and Yeast Cells Reuse", Energy and Environmental Science, No. 5, 2012, 8 pages.
Jin et al., "Two-Step SSCF to Convert AFEX-Treated Switchgrass to Ethanol using Commercial Enzymes and *Saccharomyces cerevisiae* 424A (LNH-ST)", Bioresource Technology, vol. 101, No. 21, 2010, pp. 8171-8178.
Wyman et al., "Comparative Sugar Recovery Data From Laboratory Scale Application of Leading Pretreatment Technologies to Corn Stover", Bioresource Technology, vol. 96, No. 18, 2005, pp, 2026-2032.
Wyman et al., "Coordinated Development of Leading Biomass Pretreatment Technologies", Bioresource Technology, vol. 96, No. 18, 2005, pp. 1959-1966.
Yatsu et al., "Conversion of Cellulose I to Stable Cellulose III", Textile Research Journal, vol. 56, No. 7, Jul. 1986, pp. 419-424.
Yoon et al., "Ammonia-Recyced Percolation Process or Pretreament of Biomass Feedsock", Applied Biochemistry and Biotechnology, vol. 51/52, 1995, pp. 5-19.
Yui et al,, "Structure Conversions of Cellulose III Crystal Models in Solution State: A Molecular Dynamics Study", Cellulose, vol. 17, No. 4, Aug. 2010, pp. 679-691.
Zhang et al., "The Effect of Different Treatment Conditions on Biomass Binder Preparation for Lignite Briquette", Fuel Processing Technology, vol. 73, 2001, pp. 185-196.
Zhao et al., "Organosolv Pretreatment of Lignocellulosic Biomass for Enzymatic Hydrolysis", Applied Microbial Biotechnol, 2009, vol. 82, pp. 815-827.
Zhu et al., "Cocurrent Downflow Circulating Fluidized Bed (Downer) Reactors—A State of the Art Review", The Canadian Journal of Chemical Engineering, vol. 73, Oct. 1995, pp. 662-677.
Zugenmaier, Peter, "Conformation and Packing of Various Crystalline Cellulose Fibers", Progress in Polymer Science, vol. 26, No. 9, Nov. 2001, pp. 1341-1417.
"Topic 3 R&D on Processes for Solid, Liquid and Gaseous Fuels From Biomass", 20th European Biomass Conference and Exhibition, 2012, 26 pages.
Communicaton pusuant to Article 94(3) EPC received for European Patent Application No. 07776479.3, mailed on Dec. 5, 2012, 4 pages.

Communication pursuant to Rules 161(2) and 162 EPC received or European Patent Application No. 10778488.6, mailed on Dec. 30, 2011, 2 pages.
Extended European Search Report received for European Patent Application No. 10814256.3, mailed on Jan. 23, 2013, 6 pages.
Communication pursuant to Article 94(3) EPC received for European Patent Application No. 10814256.3, mailed on Sep. 6, 2013, 4 pages.
Non-Final Office Action received for U.S. Appl. No. 11/719,158, mailed on Apr. 1, 2009, 6 pages.
Final Office Action received for U.S. Appl. No. 11/719,158, mailed on Aug. 4, 2010, 7 pages.
Notice of Allowance received for U.S. Appl. No. 11/719,158, mailed on Jan. 6, 2011, 4 pages.
Non-Final Office Action received for U.S. Appl. No. 12/229,225, mailed on Aug. 16, 2011, 6 pages.
Final Office Action received for U.S. Appl. No. 12/229,225, mailed on Jan. 6, 2012, 7 pages.
Non-Final Office Action received for U.S. Appl. No. 11/729,632, mailed on May 6, 2009, 5 pages.
Notice of Allowance received for U.S. Appl. No. 11/729,632, mailed on Nov. 16, 2009, 7 pages.
Restriction Requirement received for U.S. Appl. No. 11/897,119, mailed on Sep. 30, 2011, 6 pages.
Communication pursuant to Article 94(3) EPC received for European Patent Application No. 11162906.9, mailed on Mar. 6, 2013, 5 pages.
Communication pursuant to Rules 161(2) and 162 EPC received for European Patent Application No. 11772569,7, mailed on Nov. 30, 2012, 2 pages.
Extended European Search Report received for European Patent Application No. 11650707.8, mailed on Jul. 3, 2014, 8 pages.
Non-Final Office Action received for U.S. Appl. No. 12/226,763, mailed on Aug. 22, 2011, 13 pages.
Final Office Action received for U.S. Appl. No. 12/226,763, mailed on Jan. 10, 2012, 16 pages.
Notice of Allowance received for U.S. Appl. No. 12/226,763, mailed on May 29, 2012, 9 pages.
Notice of Allowance received for U.S. Appl. No. 12/226,763, mailed on Oct. 1, 2012, 7 pages.
Non-Final Office Action received for U.S. Appl. No. 12/791,703, mailed on Jul. 27, 2012, 7 pages.
Notice of Allowance received for U.S. Appl. No. 12/791,703, mailed on Nov. 8, 2012, 8 pages.
Restriction Requirement received for U.S. Appl. No. 12/763,102, mailed on Sep. 17, 2012, 11 pages.
Non-Final Office Action received for U.S. Appl. No. 12/763,102, mailed on Dec. 24, 2012, 18 pages.
Final Office Action received for U.S. Appl. No. 12/763,102, mailed on Aug. 5, 2013, 12 pages.
Advisory Action received for U.S. Appl. No. 12/763,102, mailed on Dec. 6, 2013, 3 pages.
Non-Final Office Action received for U.S. Appl. No. 12/976,344, mailed on Apr. 5, 2013, 12 pages.
Notice of Allowance received for U.S. Appl. No. 12/976,344, mailed on Feb. 23, 2012, 7 pages.
Notice of Allowance received for U.S. Appl. No. 12/976,344, mated on Mar. 27, 2012, 8 pages.
Non-Final Office Action received for U.S. Appl. No. 12/976,344, mailed on Apr. 1, 2014, 19 pages.
Notice of Allowance received for U.S. Appl. No. 12/976,344, mailed on Nov. 28, 2014, 10 pages.
Notice of Allowance received for U.S. Appl. No. 13/458,830, mailed on Jul. 9, 2014, 8 pages.
Notice of Allowance received for U.S. Appl. No. 13/458,830, mailed on Dec. 18, 2014, 5 pages.
Non-Final Office Action received for U.S. Appl. No. 13/591,092, mailed on Dec. 13, 2012, 13 pages.
Final Office Action received for U.S. Appl. No. 13/591,092, mailed on Mar. 25, 2013, 22 pages.
Advisory Action received for U.S. Appl. No. 13/591,092, mailed on Jun. 6, 2013, 3 pages.

(56) References Cited

OTHER PUBLICATIONS

Notice of Allowance received for U.S. Appl. No. 13/591,092, mailed on Feb. 21, 2014, 11 pages.
Notice of Allowance received for U.S. Appl. No. 13/835,766, mailed on Oct. 2, 2014, 8 pages.
Notice of Allowance received for U.S. Appl. No. 13/835,766, mailed on Jan. 28, 2015, 7 pages.
Non-Final Office Action received for U.S. Appl. No. 13/888,021, mailed on Jun. 30, 2014, 37 pages.
Final Office Action received for U.S. Appl. No. 13/886,021, mailed on Feb. 24, 2015, 31 pages.
Restriction Requirement received for U.S. Appl. No. 13/997,043, mailed on Jan. 23, 2015, 11 pages.
Restriction Requirement received for U.S. Appl. No. 13/202,011, mailed on Jul. 17, 2012, 6 pages.
Non-Final Office Action received for U.S. Appl. No. 13/202,011, mailed on Sep. 27, 2012, 8 pages.
Notice of Allowance received for U.S. Appl. No. 13/202,011, mailed on Apr. 9, 2013, 9 pages.
Notice of Allowance received for U.S. Appl. No. 13/202,011, mailed on Nov. 8, 2013, 7 pages.
Office Action received for Canadian Patent Application No. 2,650,860, mailed on Oct. 24, 2011, 3 pages.
Office Action received for Canadian Patent Application No. 2,650,860, mailed on Jun. 18, 2012, 2 pages.
Notice of Allowance received for Canadian Patent Application No. 2,650,860, mailed on Apr. 2, 2013, 1 page.
Office Action received for Canadian Patent Application No. 2,737,704, mailed on Nov. 5, 2012, 3 pages.
Office Action received for Canadian Patent Application No. 2,737,704, mailed on Feb. 21, 2013, 3 pages.
Non Final Office Action received for U.S. Appl. No. 13/997,043, mailed on Jul. 17, 2015, 16 pages.
Non Final Office Action received for U.S. Appl. No. 13/835,382, mailed on Oct. 7, 2015, 10 pages.
Non Final Office Action received for U.S. Appl. No. 13/886,021, mailed on Oct. 30, 2015, 22 pages.
Non Final Office Action received for U.S. Appl. No. 14/251,921, mailed on Nov. 16, 2015, 12 pages.
Restriction Requirement received for U.S. Appl. No. 14/251,921 mailed on Sep. 3, 2015, 6 pages.
Extended European Search Report Received for European Patent Application 141746495, mailed on Dec. 23, 2014, 8 pages.
Communication pursuant to Article 94(3) EPC received for European Patent Application No. 14174649.5, mailed on Sep. 30, 2015, 5 pages.
Preliminary Rejection received for Brazilian Patent Application No. PI0722418-4, mailed on Sep. 29, 2015, 6 pages.
Preliminary Rejection received for Brazilian Patent Application No. PI0711139-8, mailed on Sep. 29, 2015, 11 pages.
Office Action received for Mexican Patent Application No. MX/a/2014/012737 mailed on Dec. 23, 2014, 7 pages.
Office Action received for Vietnamese Patent Application No. 1-2014-03985, mailed on Feb. 13, 2015, 2 pages.
Office Action received for Canadian Patent Application No. 2,870,758, mailed on Jul. 24, 2015, 6 pages.
Dale, Bruce E, et al., "Hydrolysis of Lignocellulosics at Low Enzyme Levels: Application of the AFEX Process", Bioresource Technology, vol. 56, 1996, pp. 111-116.
Non Final Office Action received for U.S. Appl. No. 13/997,043, mailed on Apr. 18, 2016, 22 pages.
Office Action received for Brazilian Patent Application No. 0722418-4, mailed on Jan. 14, 2013, 3 pages.
Preliminary Rejection received for Brazilian Patent Application No. PI0711139-8, mailed on Jan. 22, 2016, 6 pages.
Preliminary Rejection received for Braziiian Patent Application No. PI0722418-4, mailed on Feb. 5, 2016, 4 pages. (English Translation only).
Office Action received for Canadian Patent Application No. 2,870,758, mailed on Mar. 9, 2016, 5 pages.
Office Action received for Chinese Patent Application No. 201080022215,3, mailed on Apr. 16, 2014, 7 pages (4 pages of English Translation and 3 pages).
Office Action received for Chinese Patent Application No. 201080022215.3, mailed on Nov. 6, 2014, 16 pages (9 pages of English Translation and 7 pages).
Office Action received for Chinese Patent Application No. 201080022215.3, mailed on May 5, 2015, 9 pages (5 pages of English Translation and 4 pages).
Office Action received for Chinese Patent Application No. 201080022215.3, mailed on Nov. 24, 2015, 7 pages (4 pages of English Translation and 3 pages).
Office Action received for Chinese Patent Application No. 201380022053.7, mailed on Jan. 8, 2016, 13 pages (7 pages of English Translation and 6 pages).
Office Action received for European Patent Application No. 11162906,9, mailed on Jan. 16, 2012, 2 pages.
Communication Pursuant to Article 94(3) EPC received for European Patent Application No. 10778488.6, mailed on Dec. 16, 2014, 4 pages.
Extended European Search Report Received for European Patent Application No. 15171198.3, mailed on Sep. 16, 2015, 7 pages.
First Examination Report received for Indian Patent Application No. 9645/DELNP/2011, mailed on Jan. 20, 2016, 4 pages.
First Examination Report received for Indian Patent Application No. 110/DELNP/2012, mailed on Jan. 20, 2016, 4 pages.
Search Report and Written Opinion received for Singapore Patent Application No. 11201406820T, issued on Dec. 18, 2015, 10 pages.
International Search Report and Written Opinion received for PCT Patent Application No. PCT/US10/35826, mailed on Jul. 13, 2010, 8 pages.
Tumuluru, et al., "A Review on Biomass Densification Technologies for Energy Application", Idaho National Laboratory, Aug. 2010, pp. 1-96.

\* cited by examiner

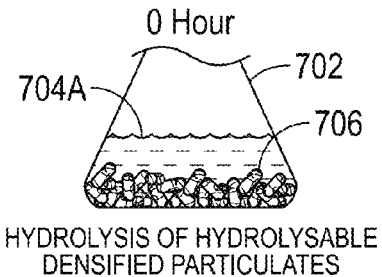

FIG. 7A HYDROLYSIS OF HYDROLYSABLE DENSIFIED PARTICULATES

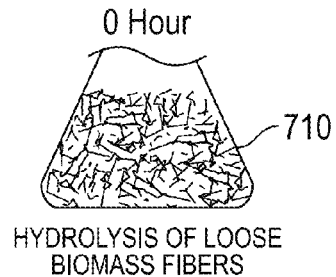

FIG. 7E HYDROLYSIS OF LOOSE BIOMASS FIBERS

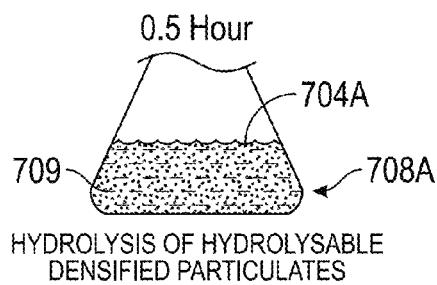

FIG. 7B HYDROLYSIS OF HYDROLYSABLE DENSIFIED PARTICULATES

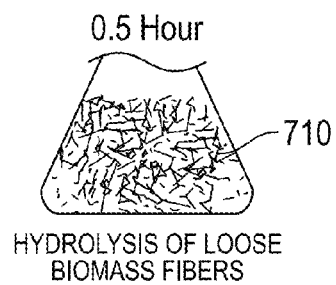

FIG. 7F HYDROLYSIS OF LOOSE BIOMASS FIBERS

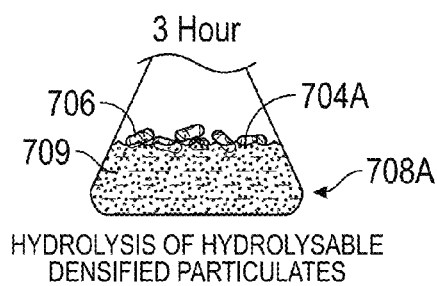

FIG. 7C HYDROLYSIS OF HYDROLYSABLE DENSIFIED PARTICULATES

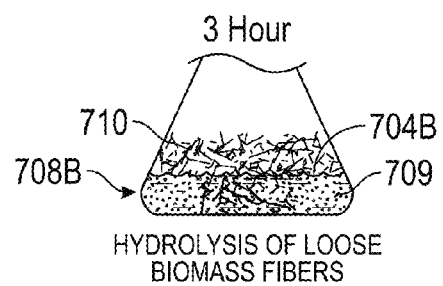

FIG. 7G HYDROLYSIS OF LOOSE BIOMASS FIBERS

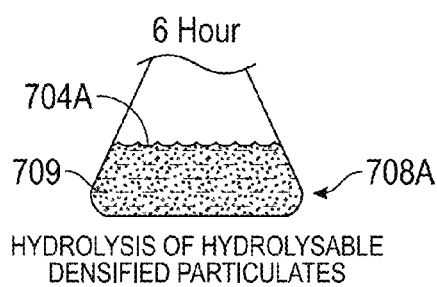

FIG. 7D HYDROLYSIS OF HYDROLYSABLE DENSIFIED PARTICULATES

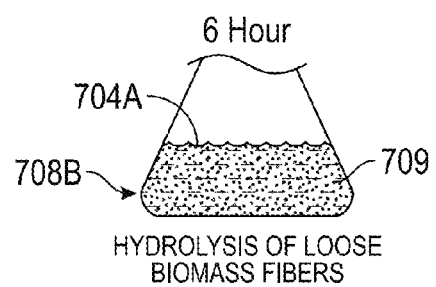

FIG. 7H HYDROLYSIS OF LOOSE BIOMASS FIBERS

METHODS OF HYDROLYZING PRETREATED DENSIFIED BIOMASS PARTICULATES AND SYSTEMS RELATED THERETO

This application is a Continuation of U.S. patent application Ser. No. 13/458,830, filed on Apr. 27, 2012, which application is a Continuation-in-Part of U.S. patent application Ser. No. 13/202,011 filed on Aug. 17, 2011, which application is a U.S. National Stage Filing under 35 U.S.C. 371 from International Application No. PCT/US2010/046525, filed Aug. 24, 2010, and published in English as WO 2011/028543 on Mar. 10, 2011, which application claims benefit under 35 U.S.C. 119 (e) of U.S. Provisional Application Ser. No. 61/236,403 filed on Aug. 24, 2009, which Applications and Publications are all hereby incorporated by reference in their entireties.

STATEMENT OF GOVERNMENT RIGHTS

This invention was made with Government support under DE-FG36-08-GO88073 and DE-FC02-07ER64494 by the U.S. Department of Energy. The government has certain rights in the invention.

BACKGROUND

Current attempts to produce cellulosic-based ethanol are cost prohibitive and involve a number of steps.

SUMMARY

In one embodiment, a product is provided comprising at least one hydrolysable densified biomass particulate having no added binder and comprised of a plurality of lignin-coated plant biomass fibers, wherein the at least one hydrolysable densified biomass particulate has an intrinsic density substantially equivalent to a binder-containing hydrolysable densified biomass particulate and has a substantially smooth, non-flakey outer surface. In one embodiment, the novel product contains trace amounts of ammonia. In one embodiment, the product comprises one or more hydrolysable densified biomass particulates, each particulate having no added binder and an amount of lignin-coated plant biomass fiber sufficient to form a hydrolysable densified biomass particulate which has an intrinsic density substantially equivalent to a binder-containing hydrolysable densified biomass particulate.

In one embodiment, the at least one hydrolysable densified biomass particulate having no added binder has an increased resistance to deformation, an increased hardness, an increased resistance to degradation, an improved shelf life, or a combination thereof, as compared with a binder-containing hydrolysable densified biomass particulate. In one embodiment, the novel product is more able to resist stress and is likely less brittle as compared to a binder-containing hydrolysable densified biomass particulate.

In one embodiment, the novel product is harder, such as at least 21% harder, with at least 20% less variability in hardness than a binder-containing hydrolysable densified biomass particulate of the same given mass.

The novel products described herein can be any suitable shape and size, including, for example, substantially rectangular or substantially cylindrical.

In one embodiment, each of the plurality of lignin-coated plant biomass fibers in the hydrolysable densified particulate is completely coated with lignin. In one embodiment, at least some of the plurality of lignin-coated biomass fibers is also coated with hemicellulose. In one embodiment, most of the plurality of lignin-coated plant biomass fibers in the hydrolysable densified particulate is also coated with hemicellulose. In one embodiment, substantially all of the plurality of lignin-coated plant biomass fibers in the hydrolysable densified particulate is also coated with hemicellulose, such that the hemicelluloses and lignin appear to come to the surface in a "package" rather than as separate components.

Any suitable plant biomass may be used to produce the novel products described herein, including, but not limited to, corn stover, switchgrass, pine and/or prairie cord grass.

In one embodiment, the novel product has an improved shelf life, increased resistance to degradation, increased flowability, and greater bulk density as compared to the binder-containing hydrolysable densified biomass particulate.

In one embodiment, a packaged product is provided comprising a container; and a quantity of hydrolysable densified biomass particulates having no added binder and located within the container, wherein the quantity of hydrolysable densified biomass particulates has a bulk density at greater than a bulk density of an identical quantity of binder-containing hydrolysable densified biomass particulates. The container may be a rigid container or a flexible bag.

In one embodiment, an integrated process is provided comprising subjecting a quantity of biomass fibers to an ammonia treatment, wherein at least a portion of lignin contained within each fiber is moved to an outer surface of each fiber to produce a quantity of tacky (i.e., sticky to the touch) biomass fibers; and densifying the quantity of tacky biomass fibers to produce one or more hydrolysable densified biomass particulates, wherein the quantity of tacky biomass fibers is densified without adding binder. In one embodiment the ammonia treatment causes at least a portion of hemicellulose contained within each fiber to move to the outer surface of each fiber. In one embodiment, the ammonia treatment is an ammonia fiber expansion (AFEX™) treatment, such as a gaseous AFEX™ treatment.

In one embodiment, the integrated process further comprises a hydrolysis step in which the hydrolysable densified biomass particulates are hydrolyzed using high solids loading, i.e., greater than 12%. Use of high solids loading results in a cellulosic sugar stream sufficiently concentrated to allow for conversion of the liberated sugars into biofuels through fermentation (e.g., at least about 6 to about 8% by weight fermentable sugars) or to an entire suite of other useful bioproducts. In one embodiment, the conversion comprises fermentation.

Various systems for producing the cellulosic sugar stream and/or the converted cellulosic biomass are also provided.

In one embodiment, a biofuel is provided comprising at least one hydrolysable densified biomass particulate of a given mass having no added binder and comprised of a plurality of lignin-coated plant biomass fibers, wherein the at least one hydrolysable densified biomass particulate has an intrinsic density substantially equivalent to a binder-containing hydrolysable densified biomass particulate of the same given mass and has a substantially smooth, non-flakey outer surface. Such a biofuel may be useful in biomass-burning stoves or boilers.

In one embodiment, an animal feed is provided, comprising at least one hydrolysable densified biomass particulate of a given mass having no added binder and comprised of a plurality of lignin-coated plant biomass fibers, wherein the at least one hydrolysable densified biomass particulate has an intrinsic density substantially equivalent to a binder-containing hydrolysable densified biomass particulate of the same given mass and has a substantially smooth, non-flakey outer surface, wherein the animal feed has improved digestibility as compared with animal feed containing binder-containing hydrolysable densified biomass particulates.

In one embodiment, a solid material is provided, comprising at least one hydrolysable densified biomass particulate of a given mass having no added binder and comprised of a plurality of lignin-coated plant biomass fibers, wherein the at least one hydrolysable densified biomass particulate has an intrinsic density substantially equivalent to a binder-containing hydrolysable densified biomass particulate of the same given mass and has a substantially smooth, non-flakey outer surface, wherein the solid material is useful in construction, such as in fiberboard or extruded fibrous building materials.

The resulting densified biomass particulates are useful in a variety of applications, including, but not limited to, the production of animal feed, an entire suite of other bioproducts using chemical catalysis or chemical conversions, other biochemical applications, biofuels, including for electricity generating applications (e.g., burning in a boiler, biomass-burning stoves, and the like), as a component in solid materials, such as fiberboards and extruded fibrous building materials, and the like.

BRIEF DESCRIPTION OF THE DRAWINGS

FIGS. 7A-7H are schematic illustrations which provide a visual comparison of a hydrolysis process using hydrolysable densified particulates (7A-7D) with a conventional hydrolysis process using loose biomass fibers (7E-7H) according to various embodiments.

DETAILED DESCRIPTION OF THE EMBODIMENTS

Figure 1:
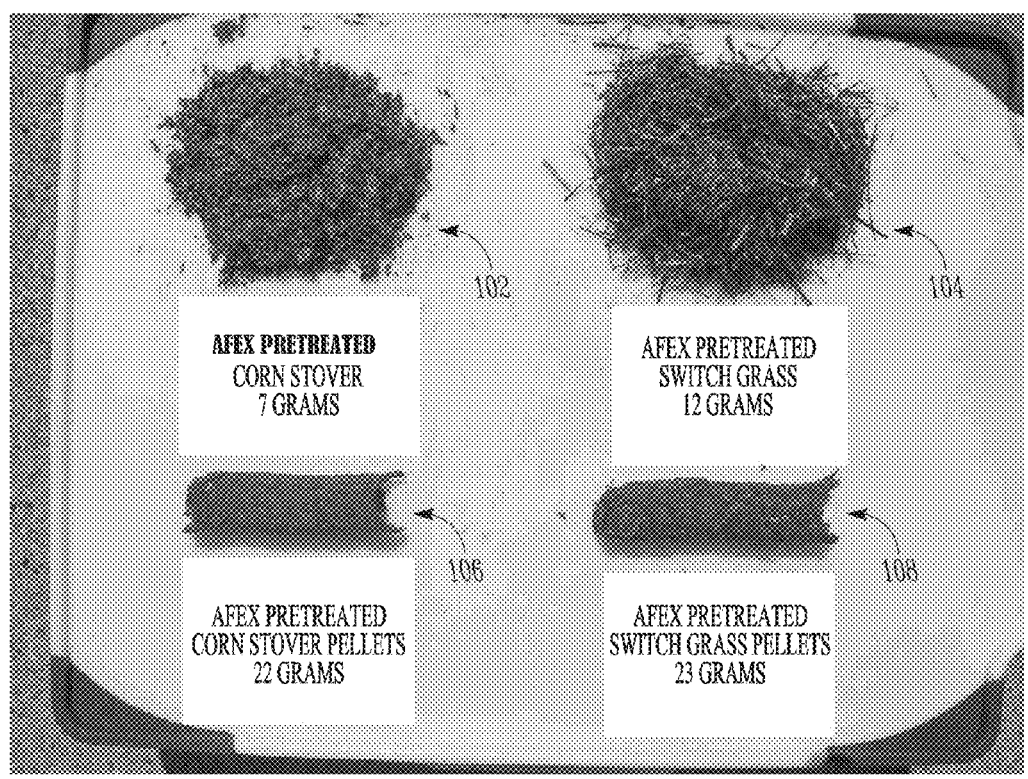
FIG. 1 comprises an image showing AFEX™ pretreated corn stover (AFEX™-CS), AFEX™ pretreated switchgrass (AFEX™-SG), AFEX™-CS briquettes and AFEX™-SG briquettes according to various embodiments.

In the following detailed description, embodiments are described in sufficient detail to enable those skilled in the art to practice them, and it is to be understood that other embodiments may be utilized and that chemical and procedural changes may be made without departing from the spirit and scope of the present subject matter. The following detailed description is, therefore, not to be taken in a limiting sense, and the scope of embodiments is defined only by the appended claims.

The term "biomass" as used herein, refers in general to organic matter harvested or collected from a renewable biological resource as a source of energy. The renewable biological resource can include plant materials, animal materials, and/or materials produced biologically. The term "biomass" is not considered to include fossil fuels, which are not renewable.

The term "plant biomass" or "ligno-cellulosic biomass (LCB)" as used herein is intended to refer to virtually any plant-derived organic matter containing cellulose and/or hemicellulose as its primary carbohydrates (woody or non-woody) available for producing energy on a renewable basis. Plant biomass can include, but is not limited to, agricultural crop wastes and residues such as corn stover, wheat straw, rice straw, sugar cane bagasse and the like. Plant biomass further includes, but is not limited to, woody energy crops, wood wastes and residues such as trees, including fruit trees, such as fruit-bearing trees, (e.g., apple trees, orange trees, and the like), softwood forest thinnings, barky wastes, sawdust, paper and pulp industry waste streams, wood fiber, and the like. Additionally grass crops, such as various prairie grasses, including prairie cord grass, switchgrass, big bluestem, little bluestem, side oats grama, and the like, have potential to be produced large-scale as additional plant biomass sources. For urban areas, potential plant biomass feedstock includes yard waste (e.g., grass clippings, leaves, tree clippings, brush, etc.) and vegetable processing waste. Plant biomass is known to be the most prevalent form of carbohydrate available in nature and corn stover is currently the largest source of readily available plant biomass in the United States. When used without a qualifier, the term "biomass" is intended to refer to LCB.

The term "biofuel" as used herein, refers to any renewable solid, liquid or gaseous fuel produced biologically and/or chemically, for example, those derived from biomass. Most biofuels are originally derived from biological processes such as the photosynthesis process and can therefore be considered a solar or chemical energy source. Other biofuels, such as natural polymers (e.g., chitin or certain sources of microbial cellulose), are not synthesized during photosynthesis, but can nonetheless be considered a biofuel because they are biodegradable. There are generally considered to be three types of biofuels derived from biomass synthesized during photosynthesis, namely, agricultural biofuels (defined below), municipal waste biofuels (residential and light commercial garbage or refuse, with most of the recyclable materials such as glass and metal removed) and forestry biofuels (e.g., trees, waste or byproduct streams from wood products, wood fiber, pulp and paper industries). Biofuels produced from biomass not synthesized during photosynthesis include, but are not limited to, those derived from chitin, which is a chemically modified form of cellulose known as an N-acetyl glucosamine polymer. Chitin is a significant component of the waste produced by the aquaculture industry because it comprises the shells of seafood.

The term "agricultural biofuel", as used herein, refers to a biofuel derived from agricultural crops, lignocellulosic crop residues, grain processing facility wastes (e.g., wheat/oat hulls, corn/bean fines, out-of-specification materials, etc.), livestock production facility waste (e.g., manure, carcasses, etc.), livestock processing facility waste (e.g., undesirable parts, cleansing streams, contaminated materials, etc.), food processing facility waste (e.g., separated waste streams such as grease, fat, stems, shells, intermediate process residue, rinse/cleansing streams, etc.), value-added agricultural facility byproducts (e.g., distiller's wet grain (DWG) and syrup from ethanol production facilities, etc.), and the like. Examples of livestock industries include, but are not limited to, beef, pork, turkey, chicken, egg and dairy facilities. Examples of agricultural crops include, but are not limited to, any type of non-woody plant (e.g., cotton), grains such as corn, wheat, soybeans, sorghum, barley, oats, rye, and the like, herbs (e.g., peanuts), short rotation herbaceous crops such as switchgrass, alfalfa, and so forth.

The term "pretreatment step" as used herein, refers to any step, i.e., treatment, intended to alter native biomass so it can be more efficiently and economically converted to reactive intermediate chemical compounds such as sugars, organic acids, etc., which can then be further processed to a variety of end products such as ethanol, iso-butanol, long chain alkanes etc. Pretreatment can reduce the degree of crystallinity of a polymeric substrate, reduce the interference of lignin with biomass conversion and by hydrolyzing some of the structural carbohydrates, thus increasing their enzymatic digestibility and accelerating the degradation of biomass to useful products. Pretreatment methods can utilize acids of varying concentrations (including sulfuric acids, hydrochloric acids, organic acids, etc.) and/or alkali such as ammonia, ammonium hydroxide, sodium hydroxide, lime, and the like. Pretreatment methods can additionally or alternatively utilize hydrothermal treatments including water, heat, steam or pressurized steam. Pretreatment can occur or be deployed in various types of containers, reactors, pipes, flow through cells, and the like. Most pretreatment methods will cause the partial or full solubilization and/or destabilization of lignin and/or hydrolysis of hemicellulose to pentose sugars.

The term "moisture content" as used herein, refers to percent moisture of biomass. The moisture content is calculated as grams of liquid, such as water per gram of wet biomass (biomass dry matter plus liquid times 100%. As such, when used without qualification herein, the % moisture content refers to a total weight basis.

The term "Ammonia Fiber Expansion" (hereinafter "AFEX™") pretreatment" as used herein, refers to a process for pretreating biomass with ammonia to solubilize lignin from plant cell wall and redeposit to the surface of the biomass. An AFEX™ pretreatment disrupts the lignocellulosic matrix, thus modifying the structure of lignin, partially hydrolyzing hemicellulose, and increasing the accessibility of cellulose and the remaining hemicellulose to subsequent enzymatic degradation. Lignin is the primary impediment to enzymatic hydrolysis of native biomass, and removal, relocation or transformation of lignin is a suspected mechanism of several of the leading pretreatment technologies, including AFEX™.

However, in contrast to many other pre treatments, the lower temperatures and non-acidic conditions of the AFEX™ process prevents lignin and/or sugars from being converted into furfural, hydroxymethyl furfural, and organic acids that could negatively affect microbial activity. The process further expands and swells cellulose fibers and further breaks up amorphous hemicellulose in lignocellulosic biomass. These structural changes open up the plant cell wall structure enabling more efficient and complete conversion of lignocellulosic biomass to value-added products while preserving the nutrient value and composition of the material. See, for example, the methods described in U.S. Pat. Nos. 6,106,888; 7,187,176; 5,037,663 and 4,600, 590, all of which are hereby incorporated by reference in their entireties as if fully set forth herein.

The term "condensed AFEX™ pretreatment" or "gaseous AFEX™ pretreatment" as used herein, refers to a gaseous AFEX™ pretreatment as defined herein, which uses gaseous ammonia rather than liquid ammonia. By allowing hot ammonia gas to condense directly on cooler biomass, the biomass heats up quickly and the ammonia and biomass come into intimate contact. Such a process is now more commonly referred to as a "GAP" process.

The term "added binder" as used herein, refers to natural and/or synthetic substances and/or energy forms added or applied to biomass fibers in an amount sufficient to improve the stability of a densified biomass particulate. Examples of commonly added binders include, but are not limited to, exogenous heat, steam, water, corn starch, lignin compounds, lignite, coffee grounds, sap, pitch, polymers, salts, acids, bases, molasses, organic compounds, urea, and tar. Specialty additives are also used to improve binding and other properties such as color, taste, pH stability, and water resistance.

Added binder in the form of added energy is typically in the form of heat which is added outright, i.e., exogenous heat, such as convective or conducted heat, although radiated heat may also be used for the same purpose. The intentional addition of exogenous heat is in contrast to intrinsic heat which develops as a result of a material being processed, such as the heat of friction which develops in densification equipment during operation. As such, heat which is inherent to the pretreatment and/or densification of biomass is not considered herein to be "added binder."

Added binder may be added to the biomass at any time before, during or after a densification process. The amount of added binder can vary depending on the substrate being densified.

The term "particulate" or "biomass particulate" as used herein refers to densified (i.e., solid) biomass formed from a plurality of loose biomass fibers which are compressed to form a single particulate product which is dividable into separate pieces. A particulate can be hydrolysable or non-hydrolysable and can range in size from small microscopic particles (larger than powders) to pellets and briquettes or large objects, such as bricks, or larger, such as hay bales or larger, with any suitable mass. The specific geometry and mass of a particulate will depend on a variety of factors including the type of biomass used, the amount of pressure used to create the particulate, the desired length of the particulate, the particular end use, and the like.

The term "briquette" as used herein refers to a compressed particulate.

The term "pellet" as used herein refers to an extruded particulate, i.e., a compressed particulate formed with a shaping process in which material is forced through a die.

The term "flowability" as used herein refers to the ability of particulates to flow out of a container using only the force of gravity. A product having increased flowability, therefore, would flow out of the container at a faster rate as compared to a product having lower flowability.

The term "logistical properties" as used herein refers to one or more properties of a particulate related to storage, handling, and transportation, which can include, but are not limited to stability, shelf life, flowability, high bulk density, high true density, compressibility, durability, relaxation, springback, permeability, unconfined yield strength, and the like.

The term "solids loading" as used herein refers to the weight percent of solids in a hydrolysis mixture comprising solids, liquid and hydrolyzing additive (e.g., enzymes). The solids can be loose cellulosic fibers or densified cellulosic particulates.

Cellulosic biofuel production from lignocellulosic biomass has gained considerable momentum due to both environmental and social sustainability benefits. However, the technology is not yet fully commercialized. One issue impeding cellulosic biofuel production using the sugar platform is the hydrolysis-resistant nature of certain components in the lignocellulosic biomass.

Nearly all forms of lignocellulosic biomass, i.e., plant biomass, such as monocots, comprise three primary chemical fractions: hemicellulose, cellulose, and lignin. Lignin which is a polymer of phenolic molecules, provides structural integrity to plants, and is difficult to hydrolyze. As such, after sugars in the biomass have been fermented to a bioproduct, such as alcohol, lignin remains as residual material (i.e., a recalcitrant lignin matrix).

Cellulose and hemicelluloses in plant cell walls exist in complex structures within the recalcitrant lignin matrix. Hemicellulose is a polymer of short, highly-branched chains of mostly five-carbon pentose sugars (xylose and arabinose), and to a lesser extent six-carbon hexose sugars (galactose, glucose and mannose). Because of its branched structure, hemicellulose is amorphous and relatively easy to hydrolyze into its individual constituent sugars by enzyme or dilute acid treatment. Cellulose is a linear polymer comprising of $\beta(1\rightarrow4)$ linked D-glucose in plant cell wall, much like starch with a linear/branched polymer comprising of $\alpha$ $(1\rightarrow4)$ linked D-glucose, which is the primary substrate of corn grain in dry grain and wet mill ethanol plants. However, unlike starch, the glucose sugars of cellulose are strung together by $\beta$-glycosidic linkages which allow cellulose to form closely-associated linear chains. Because of the high degree of hydrogen bonding that can occur between cellulose chains, cellulose forms a rigid crystalline structure that is highly stable and much more resistant to hydrolysis by chemical or enzymatic attack than starch or hemicellulose polymers. Although hemicellulose sugars represent the "low-hanging" fruit for conversion to a biofuel, the substantially higher content of cellulose represents the greater potential for maximizing biofuel yields, on a per ton basis of plant biomass.

Therefore, a pretreatment process is used to alter and open up the cell wall matrix, to hydrolyze the hemicelluloses, and to reduce crystallinity. Pretreatment disrupts the recalcitrant portions of lignocellulosic biomass, e.g., cellulose and lignin, thus improving its digestibility. After pretreatment, much of the biomass becomes easily digestible while a considerable amount remains recalcitrant. Ultimately, the pretreatment process makes the cellulose more accessible (during a subsequent hydrolysis process) for conversion of the carbohydrate polymer into fermentable sugars (Balan et al. 2008; Sierra et al. 2008; Sun and Cheng 2002). Ammonia fiber expansion (AFEX™), for example, is capable of opening up the cell wall in agricultural residues with greatly reduced degradation products compared to acidic pretreatments (Chundawat et. al., 2010), although acidic pretreatments remain a viable option.

Other pretreatment methods include, for example, ammonia recycled percolation (ARP), concentrated acid hydrolysis pretreatment, dilute acid hydrolysis, two-stage acid hydrolysis pretreatment, high pressure hot water-based methods, i.e., hydrothermal treatments such as steam explosion and aqueous hot water extraction, reactor systems (e.g., batch, continuous flow, counter-flow, flow-through, and the like), lime treatment and a pH-based treatment, hydrothermal or chemical pretreatments, followed by an enzymatic hydrolysis (i.e., enzyme-catalyzed hydrolysis) or simultaneous enzymatic hydrolysis and saccharification. As noted above, some methods generate nearly complete hydrolysis of the hemicellulose fraction for efficient recovery of high yields of the soluble pentose sugars. Recovery of these sugars also facilitates the physical removal of the surrounding hemicellulose and lignin, thus exposing the cellulose to later processing.

Although the cellulose is more available for conversion into its component sugars during hydrolysis after pretreatment, in order for fermentation to occur downstream, the resulting sugar concentration needs to be at an appropriate level (e.g., such as at least about 6% fermentable sugars by weight or, in one embodiment at least about 7% or about 8% or higher, up to about 9% or higher, such as up to about 18%, or higher, including any range there between). Some attempts to increase the sugar stream concentration include using a lower amount of pretreated biomass to produce a more dilute cellulosic sugar stream and then concentrate this stream to achieve higher sugar levels. However, concentration of the sugar stream in this manner is costly.

Additionally, since pretreated loose biomass fibers rapidly absorb liquid, use of higher amounts of loose biomass fibers, i.e., greater than 12% solids loading of biomass (e.g., 120 g of pretreated loose biomass fibers per 1 kg total weight of biomass, liquid and enzymes), or higher, produces a product which can be difficult to mix and/or does not hydrolyze efficiently. Attempts to overcome this problem include operating in batch mode by adding pretreated loose biomass fibers in small amounts, with each successive load added to the hydrolysis tank only after liquefaction of the previously added biomass fibers has been achieved. Even if the batch process comprises only two or three batches, the result is a prolonged period of initial liquefaction since serial liquefaction phases are required.

Other options to overcome this problem include using reactors and impellers which are currently regarded as "specialized" due to the size of the impellers in relation to an inner diameter of the reactor. Such reactors have impellers which have a diameter substantially the same length as the inner diameter of the reactor, i.e., an impeller size to reactor diameter ratio of greater than about 3:4. Examples include, but are not limited to, horizontal paddle mixers, horizontal ribbon blenders, vertical helical ribbons, anchor-type impellers, and the like. However, such reactors tend to be more expensive than those with smaller impellers. In addition, they are not always suitable for large vessels (>500,000 L) due to their weight.

The various embodiments provide methods for pretreating and densifying loose biomass fibers to produce hydrolysable pretreated densified biomass particulates (hereinafter "hydrolysable particulates"). In contrast to conventional densification processes, the embodiments described herein do not rely on added binder for improving the logistical properties or stability of the resulting hydrolysable particulates. Rather, and as discussed herein, the inventors have surprisingly and unexpectedly determined that highly stable and high quality hydrolysable particulates can be produced without adding binder, i.e., with "no added binder" during the densification stage, and, in various embodiments, without adding binder during the pretreatment stage before densification or at any point after densification.

Such particulates have now been shown to improve hydrolysis efficiency in terms of time and/or yield, and, ultimately, to allow conversion to occur downstream. These improvements occur, in part, because the hydrolysable particulates described herein unexpectedly allow for higher solids loading during hydrolysis as compared to loose biomass fibers, even including pretreated loose biomass fibers. A visual comparison of one embodiment of the novel hydrolysis processes described herein using hydrolysable densified particulates with a conventional hydrolysis process using loose biomass fibers, is shown in the schematic illustrations of FIGS. 7A-7H. FIGS. 7A-7H are described further in Example 8, as this visual representation also correlates with the testing performed in Example 8. Not only is the resulting sugar stream at a concentration sufficiently high to provide for effective conversion, the downstream bioproducts can now be produced more efficiently and cost effectively.

In one embodiment, the hydrolysable particulates are enzymatically hydrolyzed using a high solids loading, (i.e., a hydrolysable particulate content of greater than 12% of a combination of hydrolysable particulates, liquid and enzymes) up to about 15% or higher, such as up to about 35%, including any range there between. Use of high solids loading of hydrolysable particulates results in a cellulosic sugar stream sufficiently concentrated for conversion, such as fermentation.

Any suitable pretreatment method can be used. In one embodiment, an ammonia fiber expansion method (AFEX™) pretreatment is used.

In one embodiment, loose biomass fibers are heated to a temperature of from about 60° C. to about 100° C. in the presence of concentrated ammonia. See, for example, Dale, B. E. et al., 2004, *Pretreatment of corn stover using ammonia fiber expansion (AFEX™), Applied Biochem*, Biotechnol. 115: 951-963, which is incorporated herein by reference in its entirety. A rapid pressure drop then causes a physical disruption of the biomass structure, exposing cellulose and hemicellulose fibers, without the extreme sugar degradation common to many pretreatments.

Nearly all of the ammonia can be recovered and reused while the remaining ammonia serves as nitrogen source for microbes in fermentation. In one embodiment, about one (1) to two (2) wt % of ammonia remains on the pretreated biomass.

Additionally, since there is no wash stream in the process, dry matter recovery following an AFEX™ treatment is essentially quantitative. This is because AFEX™ is basically a dry to dry process.

AFEX™-treated biomass is also stable for longer periods (e.g., up to at least a year) than non-AFEX™-treated biomass and can be fed at very high solids loadings (such as at least about 40%) in enzymatic hydrolysis or fermentation process as compared with dilute acid or other aqueous pretreatments that cannot easily exceed 20% solids.

Cellulose and hemicellulose are also well-preserved in an AFEX™ process, showing little degradation. As such, there is no need for neutralization prior to enzymatic hydrolysis of AFEX™-treated biomass. Enzymatic hydrolysis of AFEX™-treated biomass also produces clean sugar streams for subsequent fermentation.

Degradation products from AFEX™-treated biomass have also been identified and quantified. One such study compared AFEX™ and acid-pretreated corn stover using LC-MS/GC-MS techniques. In acid-pretreated feedstock, over 40 major compounds were detected, including organic acids, furans, aromatic compounds, phenolics, amides and oligosaccharides. AFEX™ pretreatment performed under mild alkaline condition produced very little acetic acid, HMF, and furfural. See, Dale, B. E. et al., 2004, supra, and Dale, B. E. et al, 2005b, *Pretreatment of Switchgrass Using Ammonia Fiber Expansion (AFEX™) Applied Biochemistry and Biotechnology*. Vol. 121-124. pp. 1133-1142. See also Dale, B. E. et al., 2005a. *Optimization of the Ammonia Fiber Explosion (AFEX™) Treatment Parameters for Enzymatic Hydrolysis of Corn Stover, Bioresource Technology*. Vol. 96, pp. 2014-2018.

In one embodiment, a modified AFEX™ pretreatment process, i.e., a gaseous AFEX™ pretreatment is used as described in Example 1. In this method, gaseous ammonia is used, which condenses on the biomass itself.

In one embodiment, AFEX™ pretreatment conditions are optimized for a particular biomass type. Such conditions include, but are not limited to, ammonia loading, moisture content of biomass, temperature, and residence time. In one embodiment, corn stover is subject to an AFEX™ pretreatment at a temperature of about 90° C., ammonia: dry corn stover mass ratio of 1:1, moisture content of corn stover of 37.5%, and residence time (holding at target temperature), of five (5) min. In one embodiment, switchgrass is subjected to an AFEX™ pretreatment at a temperature of about 100° C., ammonia loading of 1:1 kg of ammonia: kg of dry matter, and 45% moisture content (total weight basis) at five (5) min residence time.

Hydrolysis results of AFEX™-treated and untreated samples show 93% vs. 16% glucan conversion, respectively. The ethanol yield of optimized AFEX™-treated switchgrass was measured to be about 0.2 g ethanol/g dry biomass, which is 2.5 times more than that of the untreated sample. See Dale, B. E. et al., 2005b, supra.

In one embodiment, approximately 98% of the theoretical glucose yield is obtained during enzymatic hydrolysis of an AFEX™-treated corn stover using 60 filter paper units (FPU) of cellulase enzyme/g of glucan (equal to 22 FPU/g of dry corn stover).

Ethanol yield has been shown to increase by up to 2.2 times over that of an untreated sample. In one embodiment, lower enzyme loadings of 15 and 7.5 FPU/g of glucan do not significantly affect the glucose yield, as compared with 60 FPU. In this embodiment, differences between effects at different enzyme levels decreased as the treatment temperature increased. See, for example, Dale, B. E. et al., 2004, supra; and Dale, B. E. et al., 2004, supra.

Optimal AFEX™ pretreatment conditions for hydrolysis and fermentation of switchgrass and corn stover are also discussed in Dale, B. E. et al., 2004, supra; Dale, B. E. et al, 2005b, supra; and Dale, B. E. et al., 2005b, supra.

In one embodiment, a modified AFEX™ pretreatment with significantly reduced ammonia loadings and lower required concentrations of ammonia is used. See Elizabeth (Newton) Sendich, et. al., Recent process improvements for the ammonia fiber expansion (AFEX™) process and resulting reductions in minimum ethanol selling price, 2008, Bioresource Technology 99: 8429-8435 and U.S. Patent Application Publication No. 2008/000873 to Dale, B.E.

In one embodiment, steam is used as a pretreatment instead of or in addition to an AFEX™ treatment. However, steam tends to reduce availability of sugars, thus reducing the overall quality of animal feed. Regardless, steam remains a viable optional embodiment for pretreatment.

When biomass fibers are being densified, the fibers themselves typically become hot as they are being formed into hydrolysable particulates. Such intrinsic heat can include the heat of friction which develops during an extrusion or compaction process, as is known in the art. As defined herein, such heat is not considered to be "added binder."

Although added binder is not used during the densification process as described herein, in one embodiment, added binder can be added or applied to loose biomass fibers prior to densification. Addition of liquid, such as water, during pretreatment can raise the moisture content of the hydrolysable particulates to between about 10 and about 50%.

Steam can be used in the reaction vessel prior to and/or during pretreatment, such as an AFEX™ pretreatment. Adding steam to loose biomass fibers during pretreatment may allow water to be distributed more evenly throughout the hydrolysable particulates during hydrolysis. In one embodiment, added binder is applied or added to hydrolysable particulates (i.e., after densification), although such a step can increase processing costs.

When the densification process is complete, steam evaporates off the hydrolyzed particulates, leaving a product that is sufficiently dry, i.e., typically about five (5) to about 20% moisture content, although the embodiments are not so limited.

It is to be noted that minimal amounts of the various substances and energy sources noted in the definition of "added binder" may be added at any point in the pretreatment and/or densification process and/or after the densification process in amounts that do not improve the logistical properties and/or stability of the biomass particulate, and therefore do not technically function as "added binder," as defined herein. However, such additions can increase processing costs.

Although a non-volatile base, such as sodium hydroxide, may also be used to move the lignin to the surface, the sodium hydroxide which remains after evaporation may negatively impact further application of the treated material, such as for animal feed and other applications.

Due to temperatures reaching the glass transition temperature of the oligomers within the fiber (e.g., lignin, hemicelluloses), pretreatments, such as AFEX™ (and/or steam) also transfers these oligomers (primarily lignin), and in some embodiments, an amount of hemicellulose, to the surface. Once on the surface, the lignin and hemicellulose are tacky. Surprisingly, these oligomers (lignin or lignin and hemicellulose) contain sufficient tackiness to provide properties at least comparable to that of a hydrolysable particulate which was densified with added binder (as the term is defined herein). In various embodiments, no added binder is used at any point of the process, including prior to, during or after densification.

As such, the inventors have discovered there is not only no need to apply or add "added binder" (which can also be referred to as "curing," typically through use of added steam) to the pretreated biomass (e.g., using exogenous heat) prior to forming them into hydrolysable particulates. Additionally surprising and unexpected is the discovery that there is no need to apply or add "added binder" in any form during densification (and in various embodiments, no need to apply or add "added binder" before or after densification) to produce hydrolysable particulates having logistical properties at least as good as, if not better than, conventional hydrolysable particulates containing added binder. The ability to omit the step of adding and/or applying an added binder anytime during the process, and particularly during densification, further provides significant costs savings during production, leading to a product which is not only environmentally green but highly economical and transportable, including transportable by conventional means.

In one embodiment, the densification device utilizes a gear mesh system to compress biomass through a tapering channel between adjacent gear teeth. This densification device operates at temperatures less than 60° C. (See Example 2). Such a densification device can be used to make briquettes, as the term is defined herein. In one embodiment energy consumption is minimized and physical and downstream processing characteristics are optimized.

In one embodiment, the densification device is an extrusion device which can form conventional substantially cylindrically-shaped particulates, now commonly referred to as pellets (See Example 4).

In one embodiment, an integrated biomass pretreatment and densification process is provided. In a particular embodiment, an ammonia treatment, such as an ammonia fiber expansion (AFEX™) pretreatment or condensed AFEX™ pretreatment is used in conjunction with a compaction process to produce hydrolysable particulates, in a process requiring no added binder.

In one embodiment, the hydrolysable particulates are hydrolysable briquettes having a bulk density of at least ten (10) times that of chopped biomass (which is about 50 kg/m$^3$)). In one embodiment, the hydrolysable particulates are hydrolysable pellets having a bulk density of about 550 kg/m$^3$. Use of an integrated process as described herein eliminates the need for further pretreatment at the processing plant and further minimizes the distance that low density feedstock bales need to be transported.

In one embodiment, hydrolysable particulates are transported to centralized processing facilities using existing transportation and handling infrastructure used for grains for further processing, such as hydrolyzing and/or converting (e.g., fermenting) and/or further processing, to produce various bioproducts.

In one embodiment, AFEX™ conditions are optimized according to the type of biomass being processed to enhance inherent binding properties of the loose biomass particles and increase hydrolysis efficiency following densification and storage.

It is further expected that downstream processing characteristics for briquettes will be at least as good as, or better than non-densified biomass in terms of conversion rates (e.g., fermentation rates), yields, and so forth. Indeed, and as noted herein, the improvement to hydrolysis for pellets is, unexpectedly, at least partially the result of the decreased ability of the hydrolysable particulate to absorb water.

Conventional wisdom would suggest that poor water absorption would decrease the efficiency of enzyme hydrolysis. Rather, with the decreased ability of the hydrolysable pellet to absorb water, the hydrolysable particulates are capable of moving freely within the liquid and enzyme solution at high solid loading, even after the hydrolysable pellets are fully disintegrated. In one embodiment, the hydrolysable particulates improve hydrolysis as a result of their ability to promoting mixing of the material, even at high solid loading.

In one embodiment, hydrolysis occurs in a vertically stirred reactor with an impeller size to tank diameter ratio of between 1:4 and 1:2. In one embodiment, the hydrolysis occurs in a vertically stirred reactor with an impeller size to tank diameter ratio of about 1:3, although the various embodiments are not so limited. In one embodiment, downstream conversion, such as fermentation, can also occur in such a reactor. Examples of reactors with impellers having such a ratio between impeller length and reactor diameter, include, but are not limited to, marine impellers, pitched blade turbines, Rushton impellers, and the like. This is in contrast to conventional operations not involving solid suspensions which require specialized and more expensive reactors throughout the hydrolysis and/or conversion steps.

In one embodiment, enzymatic hydrolysis is used. Any suitable enzyme capable of hydrolyzing the selected biomass can be used, including endoglucanases, cellobiohydralases, xylanases, pectinases, ligninases, swollenins, and the like.

In one embodiment, AFEX™-treated hydrolysable particulates having no added binder are provided. In contrast to conventional binder-containing particulates, the novel AFEX™-treated hydrolysable particulates described herein have a substantially smooth, non-flakey outer surface, likely due to the presence of lignin and, in some embodiments, hemicellulose, on the outer surface of the hydrolysable particulate, which essentially serve as a type of coating. As such, AFEX™-treated hydrolysable particulates are not susceptible to flaking (loss of mass) as with a conventional binder-containing particulate, which has no coating and contains removable flakes on its outer surface.

In some embodiments, the presence of lignin and/or hemicellulose is not restricted to the surface only, but also is found deeper inside the microscopic pores of the hydrolysable particulate. Therefore, the AFEX™-treated hydrolysable particulates may have added benefits, such as more efficient burning/co-firing with lignite coal than a conventional binder-containing particulate having added binder which is chemically restricted to the surface of the binder-containing particulate only.

The AFEX™-treated hydrolysable particulates are also less bendable and therefore tend to be straighter than conventional non-pretreated particulates. Surprisingly, the novel AFEX™-treated hydrolysable particulates have a harder "feel" to them (and are likely less brittle) as compared with the softer feel of a conventional non-pretreated particulate.

Hardness tests (e.g., Example 4) reveal that an AFEX™-treated pellet is stronger initially before suddenly breaking. In contrast, a conventional pellet, while maintaining strength for a longer time, is essentially more "squeezable" or "squishier" than the novel AFEX™-treated hydrolysable pellets described herein (more comparable to softness of a "cigar"). In one embodiment, an AFEX™-treated corn stover (CS) hydrolysable pellet is at least 21% harder and demonstrates at least 20% less variability in hardness as compared with a non-pretreated CS hydrolysable pellet. In one embodiment, the novel AFEX™-treated hydrolysable pellet exhibit less deformation than conventional non-pretreated CS hydrolysable pellet (See, for example, Table 7). It is likely that AFEX™-treated hydrolysable pellets, as well as AFEX™-treated hydrolysable briquette and other particulates made from other types of biomass will demonstrate similar or better results.

Lignin is generally darker than other components in plant material, so the resulting material is noticeably darker in appearance than a material not substantially surrounded by lignin.

In one embodiment, the AFEX™-treated CS pellets have a specific gravity of up to 1.16 as compared with a non-pretreated CS pellet which can have a specific gravity of no more than 0.87, although the various embodiments are not so limited. As the AFEX™-treated hydrolysable pellets appear to be less porous and further demonstrate superior hardness properties as compared with conventional non-pretreated pellets, AFEX™-treated hydrolysable pellet are likely to show improved short and long term storage properties including, flowability, compression strength, water solubility, absorption, and overall shelf life, with reduced susceptibility to degradation due to heat, bugs, and the like.

It is also expected that the AFEX™-treated hydrolysable particulates will have an improved flowability. Further testing, as noted in prophetic examples will quantify the amount of improvement.

In one embodiment, some or all of the above noted features are also present in hydrolysable particulates other than pellets (e.g., briquettes). In one embodiment, some or all of the above-noted features are additionally or alternatively present in hydrolysable particulates pretreated by methods other than AFEX™, such as with other ammonia treatments or other pretreatment methods described herein. See also Examples 6-11.

In one embodiment, the hydrolysable densified cellulosic biomass particulates are produced by subjecting a quantity of loose cellulosic fibers to a pretreatment (e.g., ammonia pretreatment) wherein at least a portion of lignin contained within each fiber is moved to an outer surface of each fiber to produce a quantity of tacky loose cellulosic biomass fibers; and densifying the quantity of tacky loose cellulosic biomass fibers to produce the one or more hydrolysable densified cellulosic biomass particulates wherein the quantity of tacky biomass fibers is densified without use of added binder. In one embodiment, the pretreating step and the densifying step form an integrated process. In one embodiment, the ammonia pretreatment is an ammonia fiber expansion (AFEX™) treatment, such as a gaseous AFEX™ pretreatment. In one embodiment, the method further comprises adding water and/or steam during the pretreating step.

In one embodiment, the hydrolysable densified cellulosic biomass particulates are produced by subjecting a quantity of loose cellulosic fibers to a pretreatment (e g, ammonia pretreatment) wherein at least a portion of lignin contained within each fiber is moved to an outer surface of each fiber to produce a quantity of tacky loose cellulosic biomass fibers; and densifying the quantity of tacky loose cellulosic biomass fibers to produce the one or more hydrolysable densified cellulosic biomass particulates wherein the quantity of tacky biomass fibers is densified without use of added binder. In one embodiment, the pretreating step and the densifying step form an integrated process. In one embodiment, the ammonia pretreatment is an ammonia fiber expansion (AFEX™) treatment or a condensed AFEX™ treatment. In one embodiment, the method further comprises adding water and/or steam during the pretreating step.

The method the bioproducts is a biofuel (e.g., ethanol or butanol).

In one embodiment, a system is provided comprising a hydrolyzing facility for hydrolyzing one or more hydrolysable densified cellulosic biomass particulates at a solids loading greater than about 12% up to about 35% to produce a convertible sugar-containing stream. The hydrolyzing facility can be part of a bioproduct production facility, such as an ethanol production facility. In one embodiment, biomass in the biomass particulates is corn stover.

In one embodiment, the system further comprises a pretreatment facility for subjecting a quantity of loose cellulosic biomass fibers to a pretreatment wherein at least a portion of lignin contained within each fiber is moved to an outer surface of each fiber to produce a quantity of tacky loose cellulosic biomass fibers; and a densifying facility for densifying the quantity of tacky loose cellulosic biomass fibers to produce the one or more hydrolysable densified cellulosic biomass particulates wherein the quantity of tacky biomass fibers is densified without use of added binder. In one embodiment, the pretreatment facility and densifying facility are co-located.

The resulting hydrolysable particulates are useful in a variety of applications, including, but not limited to, the production of animal feed, an entire suite of other bioproducts using chemical catalysis or chemical conversions (e.g., fermentation), other biochemical applications, biofuels, including for electricity generating applications (e.g., burning in a boiler, biomass-burning stoves, and the like), as a component in solid materials, such as fiberboards and extruded fibrous building materials, and the like.

The ammonia pretreatment in the various AFEX™ processes described herein dissolves a certain amount of lignin and further brings a significant amount of lignin from the interior of a plant material to the outer surface or outer edges of the fiber. As a result, the material is more easily digested by animals. In one embodiment, a combination of pretreated hydrolysable particulates, such as AFEX™-treated briquettes or pellets, as described herein, together with suitable additives and fillers as is known in the art produces a novel animal feed.

In one embodiment, a blending of the pretreated hydrolysable particulates, such as AFEX™-treated briquettes or pellets with coal provides a novel feed material in power plants.

The logistics of harvesting, handling, transporting, and storing low bulk density feedstocks pose a significant challenge to the developing bioeconomy. Assuming a yield of 70 gal/ton, biomass baled at a density 120 kg/m$^3$ would require over ten times the volume of material for a given volume of ethanol compared with corn grain. This lower bulk density will not allow trucks to reach maximum weight capacity, further increasing the number of trucks required for feedstock supply.

As the bioeconomy for alternative bioproducts develops, individual producers will need the flexibility to sell their biomass into the bioenergy market as economics warrant. For example, with use of regional biomass processing centers (RBPCs) (within a 5 to 10 mile area, for example), round bales may be transported using the existing infrastructure and equipment of the trucking industry. Because the RBPCs will be scaled appropriately, trucking distances for round bales can be minimized. Moreover, the presence of multiple, distributed RBPCs can minimize need for long term storage of round bales. Shorter term storage can use bale wraps and other current methods to minimize expense. With use of the novel integrated pretreatment (e.g., AFEX™ pretreatment)/densification system described herein, hydrolysable particulates can be more efficiently transported to centralized processing sites.

The various embodiments will be further described by reference to the following examples, which are offered to further illustrate various embodiments. It should be understood, however, that many variations and modifications may be made while remaining within the scope of the various embodiments.

EXAMPLE 1

Corn stover (CS) (everything remaining after grain is harvested, typically including stalks and leaves w/o cobs)) from a hybrid corn plant (*Zea mays* L.) grown at the Michigan State University (MSU) Agronomy Center Field was harvested in October 2007, and stored at room temperature in individual five (5) kg bags which were housed in a 30-gal trash bin. Switchgrass (SG) from the "Alamo" lowland variety of seed, *Panicum virgatum* L. grown at the Thelen Field located on Farm Lane at MSU, was harvested in October, 2005, and stored in sealed Ziploc® brand plastic bags in a freezer at four (4)° C.

The CS and SG were each subjected to an AFEX™ pretreatment comparable to the methods described in U.S. Pat. Nos. '888, '176, '663, and '590 noted above, but with certain modifications. Specifically, rather than applying liquid ammonia to the biomass and allowing the ammonia and biomass to react as in conventional AFEX™ treatment, gaseous ammonia was used instead. By allowing hot ammonia gas to condense directly on cooler biomass, the ammonia and biomass become well-mixed.

The condensation gaseous AFEX™ process pretreatment was performed in the Biomass Conversion Research Laboratory at Michigan State University, East Lansing, Mich. Unless otherwise noted, standard laboratory equipment available in conventionally stocked laboratories was used. The AFEX™ pretreatment was performed in an approved ventilation hood with protective glass sash minimum face velocity of 75 feet/minute, A Parr Instruments Model 4524 bench top reactor (hereinafter "4254 reactor") was used for this testing. The reaction chamber was first placed into the heating mantle of the 4254 reactor. A J-type T-couple temperature probe was connected to a Parr Instruments Model 4843 Modular (heat) controller (hereinafter "4843 controller") on one end and to the reaction chamber on the other end by placing the temperature probe against the internal wall of (about halfway down) the reaction chamber. The reaction chamber was then covered with a custom-fabricated circular stainless sheet metal piece having an approximately 12.7 cm (about five (5) in) diameter relief cut out for the temperature probe. The controller was turned on to low (with a red heater switch) and a J-type temperature (blue) controller showed a room temperature reading of about 25° C.±5° C.

A (yellow) K-type thermocouple (red display) and (green) Omega brand CX105 pressure connector (having offices in Stamford, Conn.) (green display) from the controller were briefly connected to test the 4254 reactor cover probes. The red display showed a room temperature reading of about 25° C.±5° C. The green display showed a one (1) atm gauge pressure reading of −0.34 to about 0.34 atm (about −5 to about 5 psig). The yellow and green connectors and 4254 reactor cover were then set aside and the blue preheat temperature was turned on to preheat the 4254 reactor to a target temperature of room temperature +20° C. The blue display was observed for about five (5) minutes to ensure that the blue temperature increased at a rate of about three (3) ° C./minute.

A Sartorius MA35 moisture analyzer (Goettingen, Germany) was used to determine the moisture content of each of the biomass samples. Initial moisture measurements for the samples were typically five (5) to ten (10) %. The weight of each sample added to the 4254 reactor was 150 g dry weight, i.e., "dry biomass." An amount of biomass was then weighed out to result in 150 g of dry biomass (as given by the total moisture calculation). For example, for a biomass sample containing five (5) % moisture content, the following calculation would be made: x (g) of water in biomass=(150 g dry biomass/(1−0.05)−150 g dry biomass). Solving for "x" results in 7.9 g of water present in the biomass. Thus, in this example, adding 150 g dry weight of biomass would include weighing and adding 157.9 g of the biomass sample at 5% moisture content.

A calculation was then made to determine the amount of deionized water to be added to each sample. For corn stover, the desired moisture content was 37.5%. For switchgrass, the desired moisture content 45%. These values were selected because they represent the optimal respective biomass moistures for maximum glucose and xylose yields from enzymatic hydrolysis after AFEX™.

Therefore, for a corn stover sample with 7.9 g of water already present, but requiring 37.5% moisture content, the following calculation would be made: x (g) water to be added to biomass=(150 g dry biomass/(1−0.375)−150 g−7.9 g water already in biomass. Solving for "x" would result in 82.1 g of water to be added. The total weight of a 150 g dry weight corn stover sample in this instance would be 82.1+g+7.9 g+150 g=240 g. Water was misted onto each biomass sample with a water bottle until the total weight (dry biomass (g)+water desired (g)) was achieved. The biomass was evenly coated with water by stirring the biomass.

An empty 500 ml ammonia cylinder having a 208 g maximum fill level (Parker 500 ml spun 316 Stainless steel pressure vessel (hereinafter "Parker cylinder") with high-pressure Swagelok® Series 83 two-way ball valves installed at both ends, made by Swagelok Co. (having offices in Chicago, Ill.) was weighed. Since eight (8) g was determined to be the approximate residual ammonia left in the cylinder after completion of this step, the total weight of the cylinder and ammonia required for AFEX™ pretreatment was determined by adding eight (8) g to the weight of the amount of ammonia needed.

The Parker cylinder was attached to an Airgas™ brand stock ammonia tank (with siphon tube) made by Airgas, Inc. (Radnor, Pa.), by opening the inlet valve on the ammonia tank, followed by opening the inlet valve on the Parker cylinder. The Parker cylinder was allowed to fill until it was cold and no more filling noise from the cylinder could be heard (elapsed time was about one (1) min). The exit valve on the ammonia tank was opened about ¼ way. After a few trials, it was determined that it took about 20 seconds to add 158 g of ammonia to the Parker cylinder. Thereafter, all valves were closed, starting with the exit valve of the Parker cylinder and finally the exit valve on the ammonia tank. The Parker cylinder was weighed to make sure the total weight was equal to the expected weight. Some ammonia was released under the hood if the weight was too great. When it was not enough, the above step was repeated.

The Parker cylinder, now containing ammonia, was heated by first wrapping it in BH Thermal brand Briskheat (Columbus, Ohio) heat tape and plugging in the BH Thermal brand Briskheat (Columbus, Ohio) heat tape controller. Cylinder pressure started at 0-125 psig (depending on the temperature of the ammonia inside the cylinder, as it became cold during the filling step). The Parker cylinder was heated to 600 psig (40 bar), adjustable from 400 psig (27 bar) for "colder" reactions (80° C.) to 1000 psig (70 bar) for hot reactions (160° C.). The pressure increased slowly, but always at a rate less than 0.034 atm/sec (five (5) psig/sec).

The desired biomass was then added to the reaction chamber. The (black) temperature probe was removed from the reaction chamber and placed into the slot on the side of the heater mantle that allowed the outside surface temperature of the reaction chamber to be measured. The (blue) display temperature was adjusted (using arrow keys) +20 degrees more than the original preheat to allow for the continued heating of the reaction chamber.

The cover of the reaction chamber was replaced and a funnel was added. The selected biomass sample was then poured down the funnel into the reaction chamber. Once added, the (yellow) temperature probe tip was completely covered with biomass and was observed to be about 2.54 cm (about one (1) in) from the ammonia input nozzle of the cover. The funnel was then removed, the cover returned on top of the 4254 reactor and brackets were tightened with bolts to seal it in place.

The Parker cylinder was then attached to the reaction chamber. A Welch Model 8803 vacuum pump. (Niles, Ill.) was also attached to the reaction chamber. The vacuum valve on the 4524 reactor was opened and the vacuum was turned on to pump air from the 4254 reactor for one (1) minute. The vacuum valve was closed and the vacuum was turn off. The (yellow) temperature probe and (green) pressure connector was plugged into the 4843 controller. The valve on ammonia cylinder (only) leading towards reaction chamber was opened.

The AFEX™ reaction was started by opening the 4254 reactor valve connected to the Parker cylinder. When the pressure between the Parker ammonia cylinder and the reaction chamber was equalized, the valves between the ammonia cylinder and the reaction chamber were closed (i.e., after about one (1) min). The heat tape on the Parker cylinder was also turned off. The 4843 reactor heater was left on a low setting at 20° C. above the original temperature used at pre-heat. After about one (1) minute the peak (red) display temperature and (green) pressure were recorded. When the (red) display temperature did not get >100° C. within 1 minute, it meant the feedstock is not touching the temperature probe. The temperature and pressure were recorded approximately every five (5) minutes thereafter.

Starting approximately five (5) minutes before expansion step noted below, the vacuum was detached from the 4524 reaction chamber cover. The ammonia cylinder pipe was removed from the reaction chamber cover. The reaction chamber was rotated so that the 4524 pressure release valve was facing toward the back of the fume ventilation hood. The ventilation hood sash was adjusted for maximum face velocity (75 feet/minute recommended). Expansion step: Ear protection was worn. The ammonia pressure in the 4524 was released by opening the pressure release valve quickly.

The reaction chamber cover was removed. The biomass was removed and placed in a tray and left under the ventilation hood to allow ammonia vapor to volatilize. The AFEX™ biomass was allowed to air-dry overnight. The Parker cylinder was weighed to determine residual grams of ammonia applied to the biomass and the weight was recorded. The remaining ammonia (approximately 8 g) was released from the Parker cylinder inside of ventilation hood.

EXAMPLE 2

Starting Materials and Sample Preparation

Corn stover (CS) obtained from the same source as described in Example 1 was used. Two samples, two (2) kg each, of each type of biomass were then subjected to the AFEX™ pretreatment according to the method described in Example 1. After pretreatment, samples were densified using a briquetting device (Federal Machine Co. d/b/a ComPAKco, LLC, Fargo, N. Dak.) to produce AFEX™ corn stover (AFEX™-CS) briquettes and AFEX™ switchgrass (AFEX™-SG) briquettes.

FIG. 1 shows an image of the four resulting products, which include seven (7) g of AFEX™-CS 102, 12 g of AFEX™-SG 104, a 22 g AFEX™-CS 106 briquette and a 23 g AFEX™-SG briquette 108). The AFEX™-CS and AFEX™ SG briquettes, 106 and 108, respectively, had a substantially rectangular shape. Both briquettes 106 and 108 were about 2.54 cm (about one (1) in) wide, about 1.27 (0.5 in) depth and about 10.16 to about 12.7 cm (about four (4) to about five (5) in) in length. (Briquette length is dependent on the particular setting use on the ComPAKco machine).

This image illustrates that just seven (7) to 12 grams of unbriquetted (i.e., loose) biomass, such as AFEX™-CS 102 and AFEX™-SG 104, occupies more space than a 22 or 23 g briquette, such as AFEX™-CS briquette 106 and AFEX™-SG briquette 108. In this instance, the unbriquetted biomass (102 and 104) occupies about 570 to about 980% more space than the briquetted biomass (106 and 108).

Figure 2:
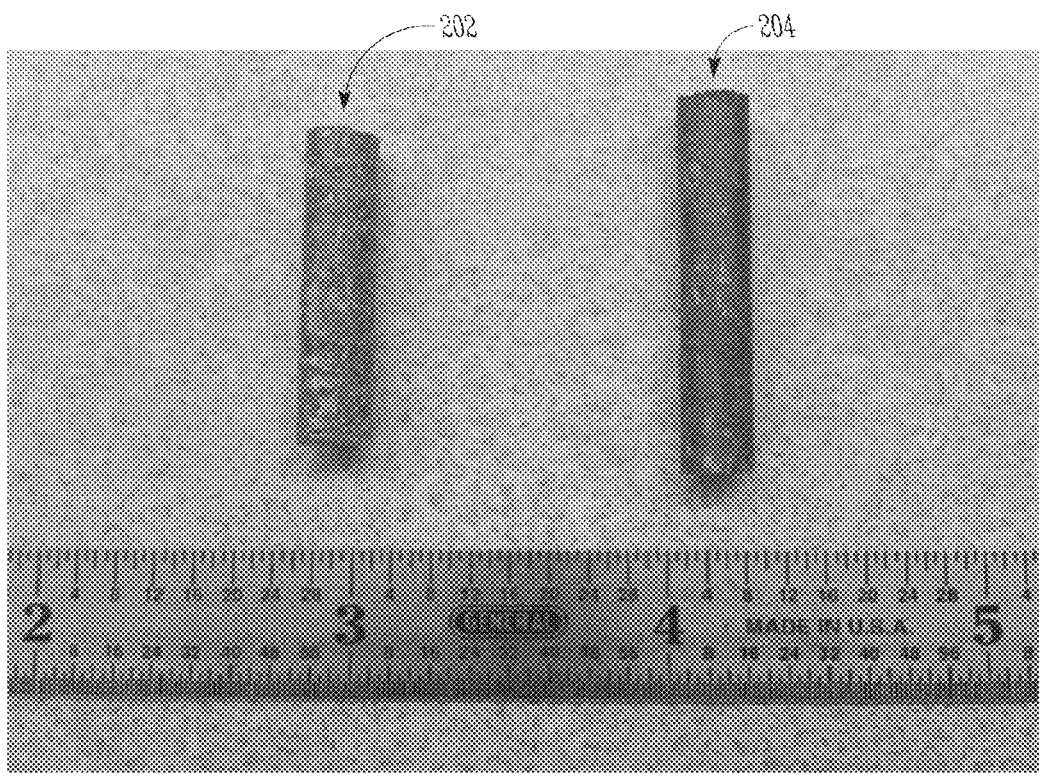
FIG. 2 comprises an image of a binder-containing non-AFEX™-CS briquette and an AFEX™-CS briquette according to various embodiments.

FIG. 2 comprises an image of a binder-containing non-AFEX™-CS briquette and an AFEX™-CS briquette according to various embodiments.

Testing Performed

Several additional samples were prepared in the manner described above and subjected to preliminary physical tests such as Angle of Repose)(° according to the method described in Carr, R. L. Jr. 1965. *Evaluating flow properties of solids*. Chemical Engineering 72(3): 163-168.

Thermal Conductivity (W/m° C.) was determined with a thermal properties meter (KD2, Decagon Devices, Pullman, Wash.) that utilized the line heat source probe technique described in Baghe-Khandan, M., S. Y Choi, and M. R. Okos. 1981, Improved line heat source thermal conductivity probe, *J. of Food Science* 46(5):1430-1432.

Water activity was measured using a calibrated water activity meter (AW Sprint TH 500, Novasina, Talstrasse, Switzerland).

Bulk density (kg/m$^3$), true density (kg/m$^3$) and porosity were determined using a multivolume pycnometer (Micromeritics model 1305, Norcross, Ga.) as described in Sahin, S. and S. G. Sumnu 2006, *Physical properties of foods*, New York, N.Y.: Springer Science Media, LLC.

Moisture Content was determined by ASAE standard method S352.1 using ISOTEMP laboratory scale (model no: 838F, Fisher Scientific, Pittsburgh, Pa.) as described in *ASAE Standards*. 51$^{st}$ ed. 2004. S352.1: *Moisture measurement—Grain and seeds*, St. Joseph, Mich.: ASABE.

Color properties (L*, a*, b*) were measured using a spectrocolorimeter (LabScan XE, Hunter Associates Laboratory, Reston, Va.).

Roundness and sphericity were determined using an Olympus SZH10 stereo microscope with a DP digital camera, followed by image analysis of the particles by Image Pro Plus® software.

Water Solubility Index (%) and Water Absorption Index (—) were calculated using the method described in Anderson, R. A., H. F. Conway, V. F. Pfeifer, and E. L. Griffin. 1969, Gelatinization of corn grits by roll and extrusion cooking, Cereal Science Today 14 (1): 4.

Results are shown in Table 1 below:

TABLE 1

Physical properties of AFEX ™-CS and SG vs. AFEX ™-CS and AFEX ™-SG Pellets*

| Biomass type | AoR (°) | TC (W/m° C.) | aw (—) | BD (kg/m$^3$) | Porosity (—) | TD (kg/m$^3$) | MC (% db) | Color L* | a* | b* | Round-ness (—) | Sphericity (—) | WAI (—) | WSI (%) |
|---|---|---|---|---|---|---|---|---|---|---|---|---|---|---|
| AFEX® switchgrass pellets | 57.4a | 0.035b | 0.575c | 547.2a | 0.487 | 918a | 13.9b | 21.7b | 2.21c | 6.47b | 0.56a | 0.64a | 6.30b | 6.74a |
| AFEX® switchgrass biomass | 56a | 0.055a | 0.787a | | 0.640a | | 29.3a | 17.8c | 2.20c | 5.94b | 0.635a | 0.52c | 6.17b | 6.14a |
| AFEX® Corn stover pellets | 60.6a | 0.04ab | 0.451b | 549.2a | 0.376b | 722b | 7.41c | 21.5b | 3.14b | 6.70b | 0.45b | 0.6b | 7.14ab | 4.36a |
| AFEX® corn stover biomass | 54.4a | 0.045ab | 0.672b | | 0.657a | | 16.7b | 24.2a | 3.69a | 8.81a | 0.56a | 0.61ab | 8.03a | 5.63a |

*Similar letters for a given property is not significantly different at α = 0.05
n = 2 for all the properties analyzed
AoR—Angle of Repose (°);
TC—Thermal Conductivity (W/m° C.);
aw—Water activity (—);
BD—Bulk density (kg/m$^3$);
TD—True Density (kg/m$^3$);
MC—Moisture Content (% db);
L*—Brightness or luminosity;
a*—redness or greenness;
b*—yellowness or blueness;
WAI—Water Absorption Index (—);
WSI—Water Solubility Index (%)

Conclusions

The AFEX™-CS briquettes (e.g., 106) and AFEX™-SG briquettes (e.g., 108), had a relatively smooth surface and held together well during handling. The AFEX™ briquettes of both the corn stover and switchgrass possess lower porosity, water adsorption index, water activity, and moisture content as compared to the non-briquetted AFEX™ samples. Such properties are an indication of improved storability for the briquetted biomass. Lower porosity, higher bulk density and higher true density of the briquettes are also indicative of reduced shipping costs.

The briquettes exhibited other desirable properties as shown in Table 1. In particular, the briquettes demonstrated a high angle of repose. A briquette's angle of repose is defined as the angle between the horizontal and the plane of contact between two briquettes when the upper briquette is just about to slide over the lower. This is also known as angle of friction. Therefore, particles have an expected value of 45 degrees. Both the corn stover briquettes and switchgrass briquettes tested herein exhibited higher than expected angles of repose of 57.4 and 60.6, respectively, as shown in Table 1. These values are likely related to the briquettes' substantially rectangular geometry.

EXAMPLE 3

The purpose of this experiment was to compare hydrolysis properties of AFEX™-CS briquettes as compared with AFEX™-CS biomass (i.e., unbriquetted).

Starting Materials

Corn stover (CS) obtained from the same source as described in Example 1 was used. An AFEX™ pretreatment was performed on the CS in the same manner as described in Example 1. Briquettes were made according to the method described in Example 2.

Tested samples included 1.7 g of AFEX™-CS biomass, a 1.6 g AFEX™-CS briquette, and a 2.2 g AFEX™-CS soaked in 100 ml amount of deionized water at 25° C. for five (5) minutes before hydrolysis to produce a soaked AFEX™-CS briquette.

Procedure

After being placed in a 500 ml beaker, an enzymatic hydrolysis was performed on each sample according to a standard laboratory protocol at one (1)% solids loading. See, for example, Shishir P. S. Chundawat, Balan Venkatesh, Bruce E. Dale, 2005, Effect of particle size based separation of milled corn stover on AFEX™ pretreatment and enzymatic digestibility, Biotechnology and Bioengineering, Vol. 96, Issue 2, pp 219-231.

Fifteen Filter Paper Units (FPU) of an enzyme, specifically Spezyme® CP (Genencor®, a Danisco Division, having offices in Rochester, N.Y. whole cellulose, was added. The samples were incubated at 50° C. in a New Brunswick incubator Innova 44, (Edison, N.J.) while being shaken at 150 RPM within the incubator. Observations and samples were taken at 6 hrs, 24 hrs and 72 hrs incubation time.

Results

Figure 3A:
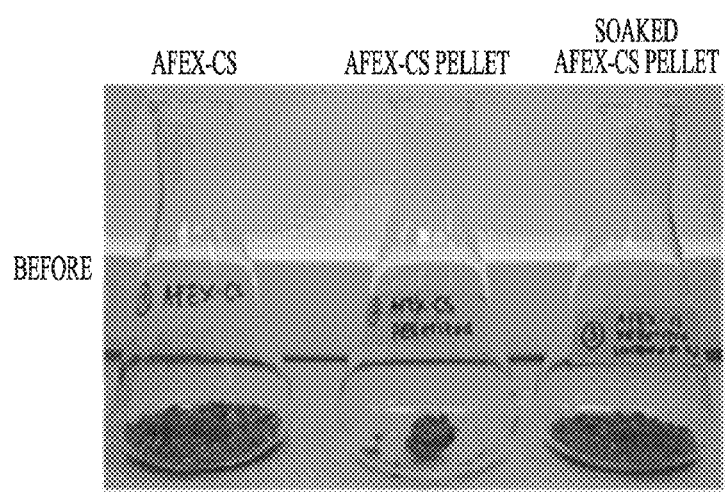
FIGS. 3A-3E are images taken at various times of three biomass samples, including AFEX™-CS, AFEX™-CS briquettes, and soaked AFEX™-CS briquettes according to various embodiments.
Figure 3B:
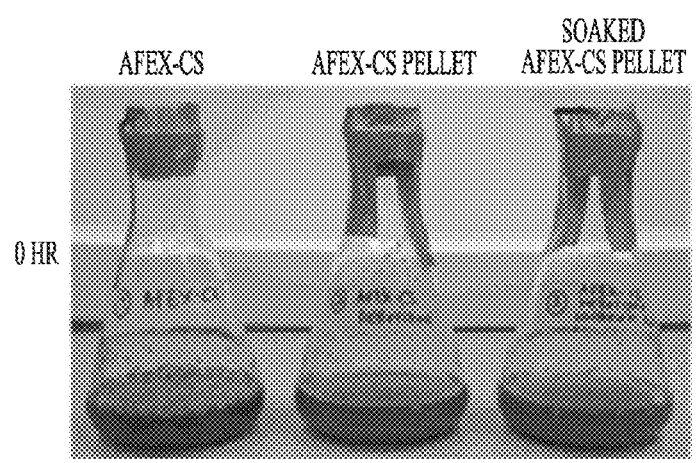
Figure 3C:
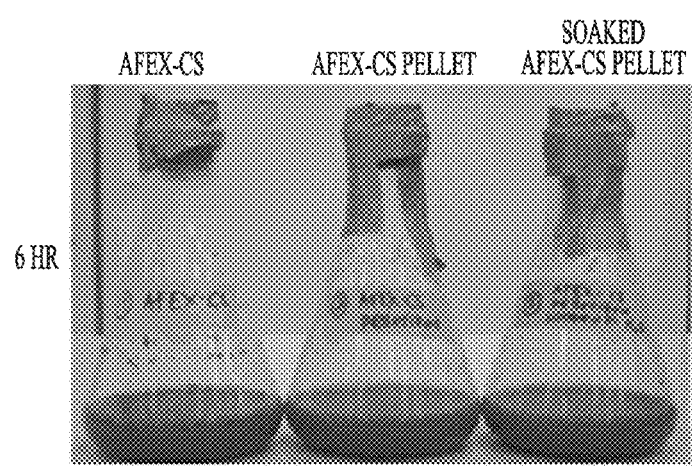
Figure 3D:
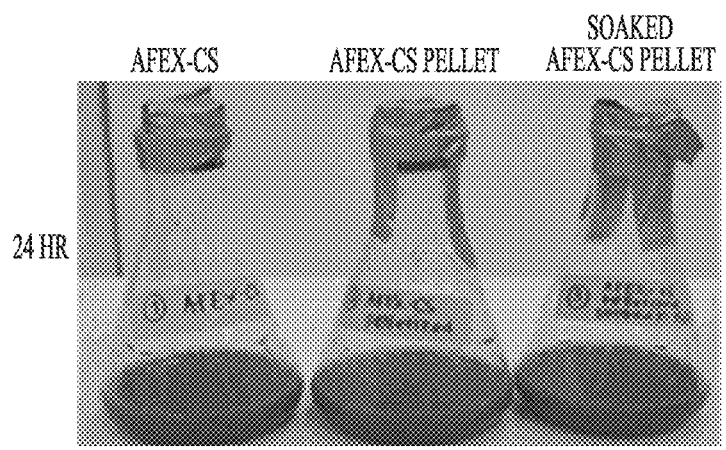

A visual inspection of the resulting hydrolysates indicates that each of the three samples completely dissolved immediately upon water addition. (FIG. 3B). Therefore, it is apparent that all three samples hydrolyzed to substantially the same extent in substantially the same amount of time.

Approximately two (2) ml samples were taken from the incubator were filtered and run through a Shimadzu high pressure liquid chromatographer (HPLC) Model LC-2010HT w/ELSD-LT to determine glucan and xylan conversions.

Figure 3E:
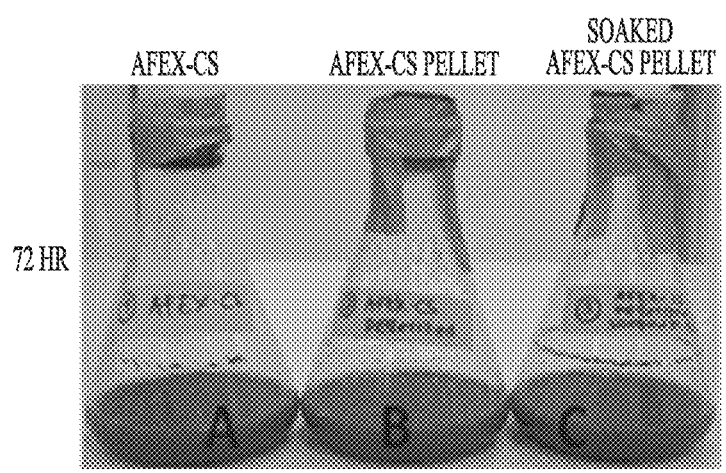
Figure 4:
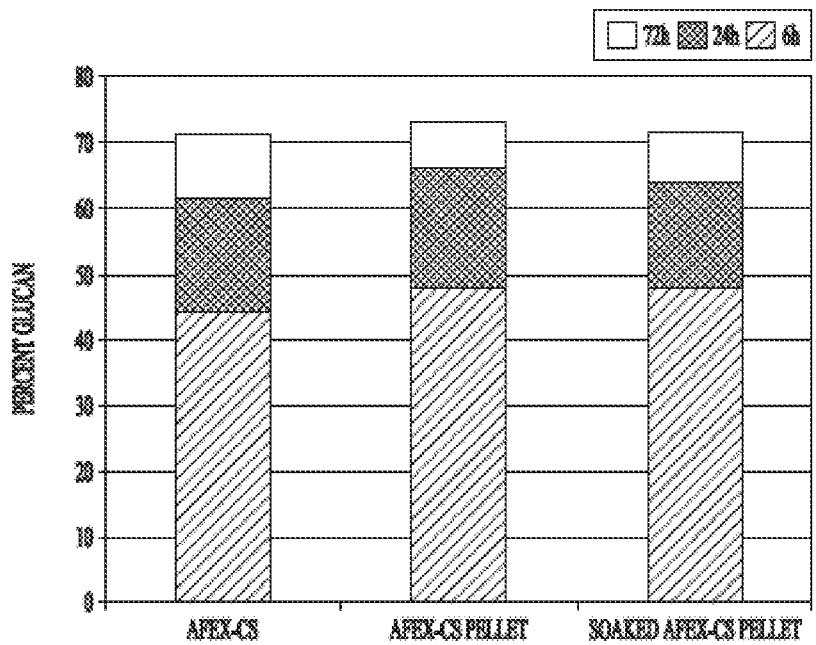
FIG. 4 is a graph show % glucan conversion versus biomass at 6 hr, 24 hr and 72 hr for the biomass samples shown in FIGS. 3C-3E according to various embodiments.
Figure 5:
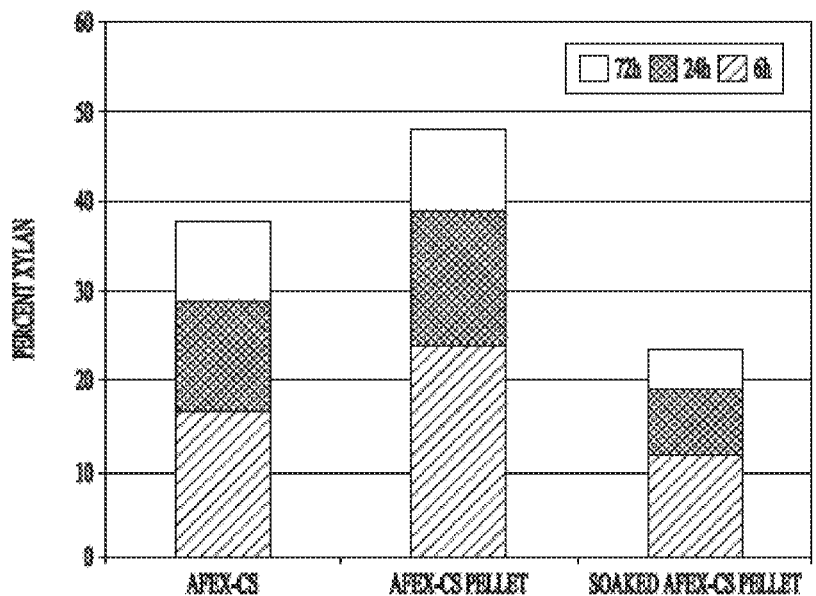
FIG. 5 is a graph show % xylan conversion versus biomass at 6 hr, 24 hr and 72 hr for the biomass samples shown in FIGS. 3C-3E according to various embodiments.

FIGS. 3A-3E are images taken at various times of three biomass samples, including AFEX-CS, AFEX-CS pellets, and soaked AFEX-CS pellets. FIGS. 4A and 4B are comparative hydrolysis graphs showing glucan conversions of the samples shown in FIGS. 3A-3E. As can be seen, the glucan conversions remain substantially the same across each sample.

Table 2 shows percent of glucan converted to glucose at various times in each of the samples.

TABLE 2

Percent of Glucan converted to Glucose

| Biomass type | % glucan conversion (to glucose) 6 h | % glucan conversion (to glucose) 24 h | % glucan conversion (to glucose) 72 h |
|---|---|---|---|
| AFEX ™ CS | 44.3 | 61.7 | 71.4 |
| AFEX ™ CS-Briquette | 48.3 | 65.9 | 73.7 |
| Soaked AFEX ™ CS-Briquette | 47.5 | 64.0 | 71.3 |

Table 3 shows the percentage of total glucose produced between samplings.

TABLE 3

Percentage of total glucose produced between samplings

| Biomass type | % total glucose 6 h | % total glucose 24 h | % total glucose 72 h |
|---|---|---|---|
| AFEX ™ CS | 44.3 | 17.4 | 9.7 |
| AFEX ™ CS-Briquette | 48.4 | 17.5 | 7.8 |
| Soaked AFEX ™ CS-Briquette | 47.5 | 16.5 | 7.3 |

Table 4 shows percentage of total xylan converted to xylose and total xylan in each sample before hydrolysis.

TABLE 4

Percentage of total xylan converted to xylose

| Biomass Type | % xylan conversion (to xylose) 6 h | % xylan conversion (to xylose) 24 h | % xylan conversion (to xylose) 72 h | Total Xylan (g) |
|---|---|---|---|---|
| AFEX ™ CS | 16.5 | 29.7 | 37.9 | 0.42 |
| AFEX ™ CS-Briquette Soaked | 24.1 | 39.6 | 48.0 | 0.38 |
| AFEX ™ CS-Briquette | 11.8 | 19.3 | 23.4 | 0.72 |

Table 5 shows the percentage of total xylose produced between samplings.

TABLE 5

Percentage of total xylose produced between samplings

| Biomass type | % total xylose 6 h | % total xylose 24 h | % total xylose 72 h |
|---|---|---|---|
| AFEX ™ CS | 16.5 | 13.2 | 8.1 |
| AFEX ™ CS-Briquette | 24.1 | 15.5 | 8.4 |
| Soaked AFEX ™ CS-Briquette | 11.8 | 7.5 | 4.0 |

Conclusion

The substantially instantaneous hydrolyzing (e.g., wetting and dispersion) in the AFEX™-CS briquette demonstrates that briquetting of corn stover biomass does not affect hydrolysis. It is likely that other AFEX™ briquettes made from other biomass materials will behave in a similar manner. Indeed, as FIG. 3B shows, most of the biomass in each briquette is converted to sugar within six (hrs), which compares favorably with the unbriquetted AFEX™-CS biomass sample. Additionally, both briquettes (AFEX™-CS briquette and the soaked AFEX™-CS briquette) hydrolyzed to nearly the same extent as the unbriquetted sample. This determination was made by observing the lack of solids remaining after 72 hours (FIG. 3E). Since the three samples had virtually the same conversions, the test was concluded at 72 hours. These results are confirmed in FIGS. 4A and 4B.

EXAMPLE 4

This test was performed to determine the comparative hardness between AFEX™-CS pellets and non AFEX™-CS pellets, i.e., pellets exposed to no pretreatment.

Starting Materials

CS obtained from the same source as described in Example 1 was used in this testing. Some of the CS was subjected to the AFEX™ pretreatment as described in Example 1. No additional treatment was performed on the AFEX™-treated biomass prior to pelleting, including no added binder and no artificial drying (any evaporation occurring in open air at room temperature is considered to be negligible during the course of the testing procedure).

The remaining portion underwent a different (non-AFEX™) procedure, which included adding approximately five (5) to ten (10) g of water per 100 g of CS to bring the moisture content of the biomass to 15% prior to pelleting.

Lodgepole pine biomass from the Driftmier Engineering Laboratory at the University of Georgia (Athens, Ga.). also underwent a similar non-AFEX™ procedure, and because the biomass moisture was measured to be greater than 15%, it was put in a dryer until it was at 12-15% moisture content.

Ten (10) AFEX™-CS pellets and ten (10) non-AFEX™-CS pellets were formed with a Yankee Pellet Machine Model 400 (Yankee Pellet Mill, Effingham, N.H.), a centrifugal die mill which produces pellets currently considered the industry standard. Ten (10) non-AFEX™ pine pellets were pelletized using a California Pellet Machine, Model CL (CPM, Crawfordsville, Ind.).

Pellets produced on both these machines have a substantially cylindrical shape and are about six (6) mm in diameter. Length can be varied as desired, but is generally more uniform than the device used above in Example 2. For purposes of testing, the pellets were about one (1) inch.

Procedure

The pellets were tested for hardness using a 12T Carver Laboratory Hydraulic Press/Hardness testing apparatus with 400 PSI gauge (Carver, Wabash, Ind.). Specifically, this test measured the amount of force needed to crush each pellet beyond its yield strength. The determination of "yield strength" was made through trained observation and "feel." Specifically, pressure was applied to each pellet until the tester observed and felt the pellet "give." Multiple pellets were tested and an average hardness, i.e., pressure required causing pellets to yield (Table 6), and average deformation (Table 7) was determined.

Results

Comparative hardness results are shown below in Table 6:

TABLE 6

Comparative Pellet Hardness for AFEX ™ and non-AFEX ™ Pellets

| non-AFEX ™ pellets (psi) | AFEX ™ pellets (psi) | Non-AFEX ™ Pine pellet |
| --- | --- | --- |
| 140 | 120 | 125 |
| 130 | 120 | 125 |
| 70 | 100 | 75 |
| 100 | 140 | 90 |
| 90 | 140 | 90 |
| 70 | 110 | 110 |
| 120 | 130 | 130 |
| 70 | 130 | 75 |
| 90 | 120 | 80 |

Measurements of the final diameter of each pellet after it "gave" were also made. These measurements are shown in Table 7. (Note that the data is randomized as compared with Table 6).

TABLE 7

Comparative Pellet Deformation for AFEX ™ and non-AFEX ™ Pellets (initial diameter: 6 mm)

| non-AFEX ™ CS pellets (mm) | AFEX ™ pellets CS (mm) | Non-AFEX ™ Pine pellet (mm) |
| --- | --- | --- |
| 5.26 | 4.66 | 5.08 |
| 4.67 | 5.28 | 5.07 |
| 4.96 | 5.28 | 5.13 |
| 4.84 | 4.98 | 5.1 |
| 5.2 | 4.73 | 5.28 |
| 5.08 | 5.18 | 4.59 |
| 4.76 | 5 | 4.75 |
| 4.15 | 5.12 | 4.61 |
| 5.39 | 5.36 | 4.98 |

The untreated, binder-added corn stover pellets average yield point was 98 psi+25 psi. The AFEX™, no binder added corn stover pellets average yield point was 119 psi+20 psi, and the non-AFEX™ binder-added pine pellet average yield point was 98 psi+23 psi.

All cylindrical pellets had a beginning diameter of 6.00 mm. The untreated, binder-added corn stover pellets average deformation at yield was 1.06 mm+0.36 mm. The AFEX™, no binder added corn stover pellets average deformation at yield was 0.95 mm+0.24 mm, and the non-AFEX™, binder-added pine pellet average deformation at yield was 1.06 mm+0.23 mm.

Conclusion

The AFEX™ pellets showed greater durability as compared to non-AFEX™ pellets. AFEX™ pellet quality is also more consistent than the non-AFEX™ pellets. As such, it is expected that any given AFEX™ pellet is less likely to be deformed or disfigured (not a cylindrical shape) as compared with a non-AFEX™ pellet.

EXAMPLE 5

This test was performed to determine the bulk density of AFEX™-CS pellets as compared to non-AFEX™ CS pellets.

AFEX™-CS pellets and non-AFEX™ CS produced according to the method described in Example 4 (about six (6) mm in diameter and about one (1) inch in length) were added to a 500 ml beaker and weighed.

The non-AFEX™ CS pellets had a bulk density of about 36 lb/ft$^3$ (553 g/L), while the AFEX™-CS pellets had a bulk density of about bout 38 lb/ft$^3$ (578 g/L).

As this preliminary test indicates, the AFEX™-CS pellets showed a higher bulk density than the non-AFEX™ CS pellets. This is likely due to their smooth non-flaky outer surface (which also is expected to improve their flowability), as compared to the rough flaky outer surface of the non-AFEX™ pellets. It is expected that a test performed on a larger scale would demonstrate an even greater difference in bulk density. Likely, the edge effects caused by the small size of the container were a significant factor in this preliminary testing.

It is also possible that pellets which are longer than the one (1) inch pellets may weigh each other down to create a higher mass at a higher density. Alternatively, shorter pellets may pack better. Additional testing (including in larger containers) will be performed to optimize pellet size, and therefore, overall bulk density, for a given application.

EXAMPLE 6

In this testing, various properties of untreated corn stover briquettes were compared with AFEX™-treated corn stover briquettes.

Starting Materials

Corn stover (CS) obtained from the same source as described in Example 1 was used. An AFEX™ pretreatment was performed on the CS in the same manner as described in Example 1. Briquettes were made according to the method described in Example 2.

Procedure

Standard procedures were followed to obtain the results shown in Tables 8 and 9. Specifically, Moisture Total: ASTM E871; Ash Content: ASTM D1102; Sulfur Content: ATSM D4239; Gross Caloric Value at Constant Volume: ASTM E711; Chlorine Content: ASTM D6721; Bulk Density: ASTM E873; Fines (Particles less than 0.32 cm (0.125 in): Twin Peaks Test CH-P-06; Durability Index: Kansas State Method; Sample above 3.8 cm (1.5 in): Twin Peaks Test CH-P-06; Maximum Length: Twin Peaks Test CH-P-06; Diameter, Range: Twin Peaks Test CH-P-05. The tumbling method used to arrive at the durability indices noted herein is known as the "Kansas State Method." See, for example, http://pelletheat.org/pdfs/StandardSpecificationWithCopyright.pdf.

Results

The results are shown below in Tables 8 and 9:

TABLE 8

Corn Stover Briquettes, Untreated

| | METHOD | UNITS | MOISTURE FREE | AS RECEIVED |
|---|---|---|---|---|
| Moisture Total | ASTM E871 | wt % | | 12.08 |
| Ash | ASTM D1102 | wt % | 4.13 | 3.63 |
| Sulfur | ASTM D4239 | wt % | 0.095 | 0.084 |
| Gross Cal. Value at Const. | ASTM E711 | Btu/lb (Btu/kg) | 8017 (17,638) | 7048 (15,506) |
| Chlorine | ASTM D6721 | mg/kg | 4218 | 3709 |
| Bulk Density | ASTM E873 | lbs/ft$^3$ (kg/m$^3$) | | 44.08 (706) |
| Fines < 0.125 in (< 0.32 cm) | TPT CH-P-06 | wt % | | 0.57 |
| Durability Index | Kansas State | PDI | | 97.9 |
| Sample > 1.5 in (3.8 cm) | TPT CH-P-06 | wt % | | 4 |
| Maximum Length (Single Briquette) | TPT CH-P-06 | in (cm) | | 1.6 (4.1) |
| Diameter, Range | TPT CH-P-05 | in (cm) | | 0.235-0.241 (0.597-0.612) |
| Diameter, Average | TPT CH-P-05 | in (cm) | | 0.239 (0.607) |
| Bag Weight | | lbs (kg) | | 3.5 (1.6) |

TABLE 9

Corn Stover Briquettes, AFEX ™

| | METHOD | UNITS | MOISTURE FREE | AS RECEIVED |
|---|---|---|---|---|
| Moisture Total | ASTM E871 | wt % | | 7.39 |
| Ash | ASTM D1102 | wt % | 4.03 | 3.73 |
| Sulfur | ASTM D4239 | wt % | 0.087 | 0.08 |
| Chlorine | ASTM D6721 | mg/kg | 3484 | 3226 |
| Bulk Density | ASTM E873 | lbs/ft$^3$ (kg/m$^3$) | | 47.15 (765) |
| Fines < 0.125 in (<0.32 cm) | TPT CH-P-06 | wt % | | 0.2 |
| Durability Index | Kansas State | PDI | | 97.9 |
| Sample > 1.5 in (3.8 cm) | TPT CH-P-06 | wt % | | 3.9 |
| Maximum Length (Single Briquette) | TPT CH-P-06 | in (cm) | | 1.85 (4.7) |
| Diameter, Range | TPT CH-P-05 | in (cm) | | 0.232-0.242 (0.589-0.615) |
| Bag Weight | | lbs (kg) | | 3.5 (1.6) |

Conclusion

As the results in Tables 8 and 9 show, the AFEX™ briquette has an increased gross caloric value, i.e., an AFEX™ briquette burns about 4.8% more efficiently due to the presence of less moisture in the AFEX™ briquette as compared with an untreated briquette. Specifically, the caloric increase, non-AFEX™ to AFEX™ was calculated as follows: 7388 Btu/lb−7048 Btu/lb=340 Btu/lb (or 748 Btu/kg); therefore % increase, non AFEX™ to AFEX™ is (340 Btu/lb)/(7048 Btu/lb)*100%=4.8%. Additionally, bulk density increased by an average of seven (7)% and there is an approximately 65% reduction in the amount of fines (i.e., broken pieces having a diameter less than 0.125 cm) in an AFEX™ briquette beg weighing about 3.5 lb (1.6 kg) as compared with a briquette bag of untreated corn stover having approximately the same weight.

Additionally, although the "durability indices" between AFEX™ and non-AFEX™ briquettes are substantially the same in this testing, the method of testing durability was a simple tumbling experiment ("Kansas State Method"), as compared with the destructive testing described in the above examples. As such, insufficient energy is provided to create the separation required to be able to properly distinguish between the briquettes. Regardless, a high durability indice shows that the AFEX™ briquettes are suitable for use in the briquette industry.

EXAMPLE 7

This test was performed to determine the water absorption capacity of pelleted AFEX™-treated corn stover compared to non-pelletized AFEX™-treated corn stover.

Conventional multi-pass, low cob corn stover was harvested and baled by Iowa State University (ISU) on Oct. 23, 2011. The stover was sourced from a field located at the GPS coordinates of 42.21 North, −93.74 West). Following grain harvest, the corn stover was windrowed using a Hiniker 5600 Series side discharge windrowing stalk chopper, and baled using a Massey Ferguson MF2170XD large square baler. The bales were stored under tarps and then milled to an approximately one-inch particle size using a Vermeer BG 480 mill. The baled corn stover was then dried to a less than 5% moisture content.

Corn stover was also obtained from a blend of multiple sources, with the predominant source being the National Renewable Energy Laboratory as provided by a farm in Wray, Colo., in 2002 as chopped corn stover. The corn stover was dried and then ground in a Wiley Mill (Thomas Scientific, Swedesboro, N.J.) to an approximately 5 mm particle size prior to use.

AFEX™ pretreatment was performed on the two corn stover samples. by packing each at a density of 100 g dry matter per L into a vertical pressure vessel (hereinafter "vessel") having an inner diameter of 10 cm r and a height of 90 cm. The moisture level with was adjusted by adding distilled water to increase the moisture content to about 25%. The resulting bed of corn stover was heated by introducing saturated steam at 10-15 psig and a mass flow rate of 1 gram per second into the top of the vessel and venting at the bottom for approximately 10 minutes. The final moisture content of the corn stover was approximately 40%.

The bottom of the vessel was sealed while compressed anhydrous ammonia vapor was introduced into the top. Maximum pressure during this ammoniation step reached 200 psig. Ammonia was added until a ratio of 1:1 ammonia: dry corn stover was achieved. The temperature of the corn stover was about 80 to about 100° C. initially and gradually decreased to about 30 to about 50° C.

After a residence time of approximately 30 minutes, the pressure was released from the vessel by allowing vapor to flow out through the bottom. The residual ammonia was then removed from the corn stover by introducing steam at a mass flow rate of 1 gram per second into the top of the vessel while venting from the bottom. After approximately 20 minutes, the steam flow was stopped and the corn stover removed from the vessel. The AFEX™-treated corn stover was then dried in a 50° C. convection oven (Blue M Electric Company Class A Batch Oven, Blue Island, Ill.).

Pelletization was performed using a Buskirk Engineering (Ossian, Ind.) PM610 flat die pellet mill (hereinafter "pellet mill"). A die with 0.25 in diameter circular holes was used. Tap water was added to the AFEX™-treated corn stover and mixed by hand until the desired moisture content was obtained. Three samples of corn stover weighing between about 3 and about 5 kg were manually added to the pellet mill at a rate sufficient to keep a mat of corn stover on the die. A roller then pressed the corn stover through the die, producing pellets. The pellets were collected and dried in the Blue M convection oven.

Samples Nos. 1 and 2 comprised the corn stover supplied from Colorado, milled to 5 mm particle size, and pelletized at 12% moisture and 50% moisture, respectively. Samples Nos. 3 and 4 were the 1-inch corn stover obtained from ISU and pelletized at 20% moisture and not pelletized, respectively.

Samples were added to distilled water at 250 g total weight in a 500 mL Erlenmeyer baffled flask and placed in a 50° C. shake flask incubator overnight to absorb water and disrupt the pellet shape. The moisture content for pelletized and loose biomass was measured using an OHaus (Parsipanny, N.J.) MB25 moisture analyzer. For the pelletized samples (Nos. 1-3), 37.5 g dry weight of the corn stover Samples was added to each flask, while 25 g dry weight of corn stover was added for Sample No. 4. Distilled water was added to each flask to increase the total weight to 250 g. After soaking overnight, the samples were removed and filtered through a Whatman #1 cellulose filter via vacuum filtration.

Once all liquid was drained, the vacuum was turned off. The volume of liquid was then measured. The water absorption capacity was measured as the difference between the final volume of recovered liquid and the total volume of water added. This measurement allowed for the calculation of free liquid (as a percentage of the total weight of components) present at 15% solids in the initial stage of hydrolysis assuming complete mixing. The results are shown in Table 10.

TABLE 10

Water absorption capacity of AFEX ™-treated corn stover

| Sample No. | Type/moisture content | Water absorbed per g biomass | Free liquid at 15% solids loading |
|---|---|---|---|
| 1 | Pellet/12% | 4.5 g | 18% |
| 3 | Pellet/20% | 3.9 g | 26% |
| 4 | Non-pelletized/ 5% moisture | 5.7 g | Trace |

These results demonstrate that pelletized corn stover at varying moisture contents can be added to water at 15% solids loading and allow the water to retain between about 18 and about 26% of its total mass as liquid. The amount of free liquid is considerably increased in the pellet produced using 1 inch particle size corn stover (Sample No. 3) compared to pellets produced at the 5 mm particle size. This may be due to increased compression of larger particle size corn stover through the die, which decreases capillary volume within the corn stover and thus decreases moisture absorption capacity. This amount of free liquid can ensure that the solids remain in suspension, which will allow for even mixing for downstream processes, such as hydrolysis.

EXAMPLE 8

This testing was performed to determine the bulk density and shelf life of pelletized, AFEX™-treated corn stover as well as the impact of mixing on the initial rate of hydrolysis.
Storability and Bulk Density Corn stover was sourced, AFEX™-treated, and densified in the manner described in Example 7. In addition to the previously described pellets, pellets were also produced at a moisture content of 25% and 35% from the AFEX™-treated corn stover obtained from Wray, Colo., and milled through a 5 mm screen.

After pelletization, about 10 g of the pellets were placed in a sealed plastic bag and observed over the course of one month. In addition, pellets dried to less than 15% moisture content were sealed in plastic containers and also observed over the course of one month. Samples were considered to have sufficient shelf life if no visible fungal growth occurred. The remaining pellets were dried in the 50° C. convection oven described in Example 7 until a moisture content of less than 15% was obtained.

Bulk density was measured by placing the dried pellets in a 1000 mL beaker. The beaker was lightly shaken to ensure even settling of pellets and weighed using a balance with a sensitivity of 0.01 g (OHaus GT 4000). Bulk density of the pellets was calculated as (total weight−beaker weight)*(1−moisture content)/1 L.

Pellets produced at 50% moisture content and placed in the plastic bag began to show signs of fungal growth after 24 hours. Within 7 days, the pellets were completely coated in a white fungus. Pellets produced at 35% moisture content and placed in plastic bags began showing fungal growth within 3 days. Within 7 days, the pellets were completely coated in a white fungus. In comparison, pellets produced at 12%, 20%, and 25% moisture contents did not appear to have any fungal growth occur for at least one month.

Likewise, when pellets were dried to less than 20% moisture content, all samples appeared to have no fungal growth for at least one month.

Figure 6:
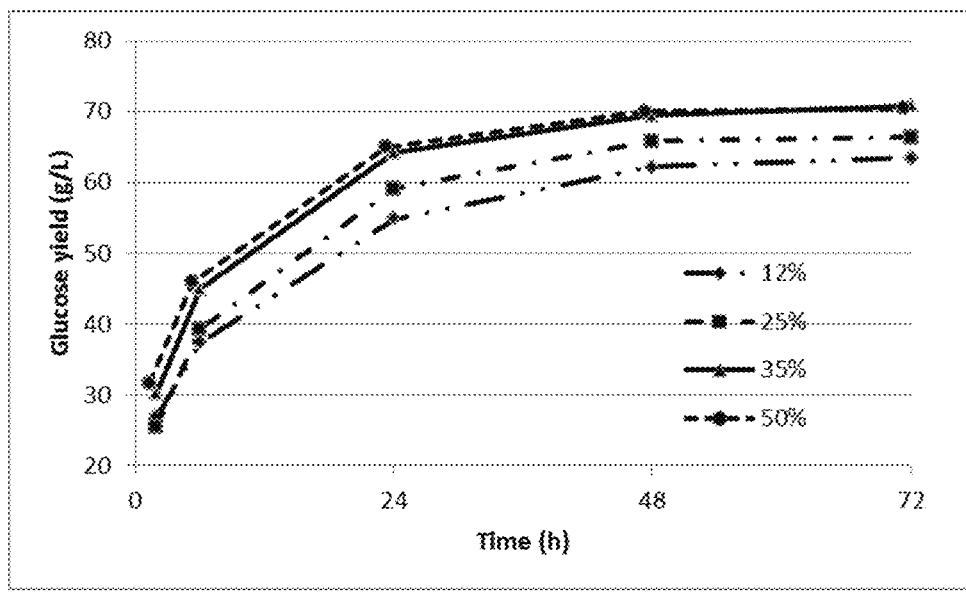
FIG. 6 is a graph showing glucose concentrations for AFEX™-treated corn stover pellets produced at four different moisture contents according to various embodiments.

Bulk density of the pellets, together with untreated loose corn stover and AFEX™-treated loose corn stover as controls, are shown in FIG. 6. As FIG. 6 shows, the bulk density of the pellets increased from 50 g/L for untreated corn stover to nearly 600 g/L for material pelleted at 12% moisture content. Corn stover pelleted at higher moisture contents saw a significant decrease in bulk density, although the bulk density was still greater than for conventional bales (120 kg/m$^3$) and the loose AFEX®-treated corn stover which had a bulk density of ~80 kg/m$^3$.

With respect to bulk density, AFEX™-treated corn stover pellets can be produced at any moisture content between 12 and 50% total weight basis, and can be produced at particle sizes ranging from 2 mm to 25 mm (1 inch), and maintain a bulk density above 200 kg/m$^3$. It is possible that pellets can be produced at even higher and/or lower moisture contents. However, dryer pellets provide a higher bulk density and longer term storability.

Impact of Mixing on Rate of Hydrolysis

The one-inch corn stover obtained from ISU was used. In addition, identical corn stover was obtained and AFEX™-treated, but not pelletized.

For Samples No. 1, 2, and 3, enzymatic hydrolysis was performed at 18% solids loading. Hydrolysis was performed in 2.8 L baffled Erlenmeyer flasks. To each flask, 500 mL of 0.1 M sodium citrate/citric acid buffer (Sigma Aldrich, St. Louis, Mo.) at pH 4.5 was added. Novozymes CTec2 cellulasic enzyme and Novozymes HTec2 hemicellulasic enzyme was added to each flask at a protein level of 1260 mg and 540 mg, respectively (7 mg and 3 mg per g corn stover). Distilled water was added to bring the total weight of the solution up to 1000 g minus the weight of 180 g dry weight of corn stover.

For Sample No. 4, enzymatic hydrolysis was performed at 24% solid loading. Hydrolysis was performed in a 125 mL baffled Erlenmeyer flask. To each flask, 25 mL of 0.1 M sodium citrate/citric acid buffer (Sigma Aldrich, St. Louis, Mo.) at a pH of 4.5 was added. Novozymes CTec2 cellulasic enzyme and Novozymes HTec2 hemicellulasic enzyme was added to each flask at a protein level of 84 mg and 36 mg, respectively (7 mg and 3 mg per g corn stover). Distilled water was added to bring the total weight of the solution up to 50 g minus the weight of 12 g dry weight of corn stover.

In Sample No. 1, unpelletized AFEX™-treated corn stover was added in a fed batch manner, with half (90 g dry weight) of the material added at the beginning of hydrolysis and half (90 g dry weight) added after 3 hours. In Sample No. 2, unpelletized AFEX™-treated corn stover was all added immediately (180 g dry weight). In Sample No. 3, pelletized AFEX™-treated corn stover was all added immediately (180 g dry weight). In Sample No. 4, pelletized AFEX™-treated corn stover was added in a fed batch manner, with half (6 g dry weight) added at the beginning of hydrolysis and half (6 g dry weight) after 3 hours. After the first biomass addition, the flasks were placed in a shake flask incubator at 50° C. and rotated at 200 RPM. The samples were inspected visually every hour and manually swirled to determine the flowability of the liquid medium and the ability to suspend biomass particulates.

A 1 mL sample was obtained at 6 hours and 24 hours after enzyme addition and analyzed for sugar production via HPLC. A Biorad (Hercules, Calif.) Aminex HPX 87P column was used to separate individual sugars at a flow rate of 0.6 mL/min and with the column heated at 85 C. A Waters 2414 refractive index detector (Milford, Mass.) was used to quantify the sugars.

A visual representation of an exemplary hydrolysis that can be performed according to the various embodiments described herein, such as the hydrolysis performed in this example, is shown in FIGS. 7A-7H. Hydrolysis of hydrolysable densified particulates 706 (e.g., Sample No. 3) is shown in FIGS. 7A-7D. The hydrolysis begins at 0 hrs, as shown in FIG. 7A with a number of hydrolysable densified particulates 706 placed in a container 702 with an amount of liquid, such as water, having a water line 704A. Within 0.5 hours, as shown in FIG. 7B, a suspension 708A is formed containing particles 709, with no hydrolysable densified particulates 706 visible above the water line 704A. The particles remain in suspension throughout the first 6 hours of hydrolysis and beyond, as shown in FIGS. 7C and 7D. If desired, additional hydrolysable densified particulates 706 can optionally be added at the 3 hr point to increase the solid loading further (e.g., Sample No. 4), as shown in FIG. 7C.

In contrast, during a conventional hydrolysis of loose biomass fibers (e.g., Sample No. 2), as shown in FIGS. 7E-7H, the loose biomass fibers and liquid, such as water, immediately combine to form wet loose biomass fibers 710 as shown in FIG. 7E, with no mixing occurring, even at the 0.5 hr point, as shown in FIG. 7F. By the 3 hr point as shown in FIG. 7G, a water line 704B is visible for the first time. For a comparable amount of starting materials, this water line 704B is lower than the water line 704A shown in FIGS. 7A-7D, i.e., when hydrolysable densified particulates 706 are used as the substrate.

Despite the eventual presence of free water as shown in FIG. 7G, the suspension 708B containing particles 709 is impeded by the presence of the unmixed wet loose biomass fibers 710 present both above and below the water line 704B. At the 6 hr point, however, as shown in FIG. 7H, the wet loose biomass fibers 710 have become sufficiently hydrolyzed such that all solids (710) have now been converted to particles 709 which remain in the suspension 708B, comparable to FIG. 7D, although the sugar concentration in the suspension 708B is lower.

As these schematics demonstrate, not only does hydrolysis occur faster initially with the hydrolysable densified particulates 706, but additional hydrolysable densified particulates 706 can optionally be added after a relatively short time period, such as no more than about half-way through a hydrolysis cycle, i.e., a higher solids loading is possible, such that the resulting suspension 708A of FIG. 7D has a higher sugar concentration as compared to the sugar concentration of suspension 708B of FIG. 7H.

Table 11 displays visual observations of the dissolution of biomass during the first 6 hours after enzyme addition for Samples No. 1, 2, and 3.

TABLE 11

Observations on mixing ability during the first 6 hours of enzymatic hydrolysis for pelleted and non-pelleted AFEX™-treated corn stover.

| Time | Sample 1 | Sample 2 | Sample 3 |
|---|---|---|---|
| 0 hour | Standing water observed, but pile of biomass was not free floating | Very large pile of biomass, no standing water was observed. Biomass could not be mixed. | Pellets completely submerged |

TABLE 11-continued

Observations on mixing ability during the first 6 hours of enzymatic hydrolysis for pelleted and non-pelleted AFEX™-treated corn stover.

| Time | Sample 1 | Sample 2 | Sample 3 |
|---|---|---|---|
| 1 hour | Slurry was very thick and difficult to mix, but all biomass was submerged in water | No visible change in appearance. No standing water observed | Mixture of pellets and free biomass. Easily swirled and not viscous |
| 2 hour | Material is easily mixed, but more viscous than with pellets. All biomass submerged. | Small amount of standing water observed. Biomass pile shrank slightly in size as particles are liquefied. Cannot be mixed by swirling. | Pellets completely disrupted. Easily swirled and not viscous |
| 3 hour | Easily mixed before second addition of biomass. After biomass addition, some biomass was above the water line. Very thick and not flowable when swirled. | Biomass pile continues to shrink in size. Small amount of standing water observed. Mixing is not possible by swirling. | No visible change |
| 4 hour | All biomass was below the water line, but still thick. Reasonably flowable and can be mixed by swirling. | Most of the biomass is now below the water line, which is now at the same height as the other two samples. Still very viscous and difficult to swirl. | No visible change |
| 5 hour | Hydrolysate is in suspension and easily mixed. | All biomass is below the water line. Sample can be mixed by swirling, but still viscous compared to the fed batch sample | No visible change |
| 6 hour | No visible change. Glucose concentration is 36.7 g/L | Hydrolysate is in suspension and easily mixed. Glucose concentration is 31.1 g/L. | No visible change. Glucose concentration is 40.7 g/L. |
| 24 hours | Easily mixable. Glucose concentration is 49.5 g/L | Easily mixable. Glucose concentration is 46.4 g/L | Easily mixable. Glucose concentration is 54.4 g/L |

These results show that use of densified corn stover significantly improves the initial phase of hydrolysis. The glucose released in the first six hours was 31% higher than for the loose biomass without fed batch addition and 11% higher than the loose biomass with fed batch addition. The improved hydrolysis performance continued through 24 hours. Furthermore, the pellet hydrolysate remained at a low apparent viscosity and was easily mixed throughout the first 6 hours, suggesting that a standard impeller could keep the biomass in suspension. Because the biomass was able to easily stay in suspension, the solid loading could easily be increased. In Sample No. 4, the biomass stayed in suspension and was easily mixed throughout the first 6 hours despite the increased solid loading. A glucose concentration of 71 g/L was obtained after 24 hours, a 30% increase over pellets at 18% solid loading.

In comparison, the fed batch hydrolysis was not easily mixable in the first hour of hydrolysis as well as the first hour after a second addition of enzymes. The loose biomass without fed batch addition remained unmixable for up to 5 hours.

EXAMPLE 9

This test was performed to determine if an 18% solid loading hydrolysis with AFEX™-treated corn stover pellets could be performed in a vertical stirred tank reactor with impeller size to tank diameter ratio of 1:3.

Corn stover was AFEX™-treated and pelletized in the manner described for Sample No. 1 in Example 7. A glass 6 liter Microferm reactor (New Brunswick Scientific, Enfield, Conn.) equipped with a six bladed Rushton impeller and a three blade marine impeller was used. The impeller diameter was about 7.5 cm and the tank inner diameter was about 21.5 cm, for an impeller size to tank diameter ratio of 0.35, or about 1:3. Four evenly spaced vertical baffles were also present in the reactor. Distilled water and enzymes were added to a total weight of 4.60 kg. Enzymes used were Novozymes CTec2 at 7,000 mg and HTec2 at 3,000 mg. Approximately 1 kg dry weight of pellets was added to the solution. Temperature was maintained at 50° C. and pH was manually adjusted to 5 using 4 M NaOH (Sigma Aldrich, St. Louis, Mo.). The impellers were spun at 400 rpm. Visual observations were recorded throughout the first 30 minutes of hydrolysis, and 20 mL samples were obtained at 1, 4, and 6 hours after the addition of pellets. These samples were quantified for sugar analysis according to the previous example.

After 48 hours of hydrolysis, the hydrolysate broth was centrifuged to remove the biomass particulates. The supernatant was then fermented using *Zymomonas mobilis* AX101 as the fermenting organism. The pH was adjusted to 6 and the temperature decreased to 30° C. *Z. mobilis* was grown on yeast extract and added to the hydrolysate at an initial OD at 600 nm of 1. Corn steep liquor at 1% (v/v) loading and potassium phosphate at 2 g/L were also added as nutrients. Samples were taken at 24 hours after inoculation to assess ethanol production and sugar utilization. Samples were analyzed for ethanol production and sugar consumption via HPLC as described in Example 8. For ethanol production, a BioRad Aminex 87H column was used instead of Aminex 87P.

The corn stover pellets were immediately suspended when agitation was initiated, and rapidly broke down to individual particulates within 10 minutes. As the pellets were disrupted, a layer of corn stover was deposited along the surface of the vessel. This layer appeared to be thin and not permanent, as sections were continually breaking off and re-entering suspension. Within 20 minutes, all of the corn stover was suspended and remained suspended for the 48 hour duration of hydrolysis. Glucose concentration was 21.9 g/L, 34.2 g/L, and 44.1 g/L after 1, 4, and 6 hours, consistent with the performance in shake flasks.

Glucose and xylose titer were 51.6 g/L and 24.3 g/L at the onset of fermentation. After 24 hours, glucose was completely consumed, and xylose was partially consumed to a final concentration of 13.1 g/L. This partial consumption is common for fermentation of AFEX™-treated corn stover with this microbe, see Lau M W et al., Biotechnology for Biofuels 3:11 (2010) as an example. Final ethanol concentration was 32.3 g/L.

As demonstrated, enzymatic hydrolysis and fermentation can be performed at levels as high as 18% solids loading, while still achieving final ethanol concentrations in excess of 30 g/L. An impeller size to tank diameter ratio of about 1:3 was sufficient to keep the solids in suspension and allow even mixing. It is likely that even higher solids loading can be used, although further testing will be performed to confirm this hypothesis.

EXAMPLE 10

In this test, pellets produced at different moisture contents were hydrolyzed at high solids to determine its impact on resulting glucose yields.

Corn stover was obtained from multiple sources but predominantly Wray, Colo., as described in Example 7. This corn stover was milled to a 5 mm particle size, AFEX™-treated, and pelleted as described in Example 7. Pellets were produced at 12% moisture, 25% moisture, 35% moisture, and 50% moisture content. Enzymatic hydrolysis was performed at 18% solid loading in 250 mL Erlenmeyer flasks at 100 g total weight. Eighteen grams (dry weight) of pellets were added to each flask, with water added in an amount to result in a total weight of 100 g for all components added.

Figure 8:
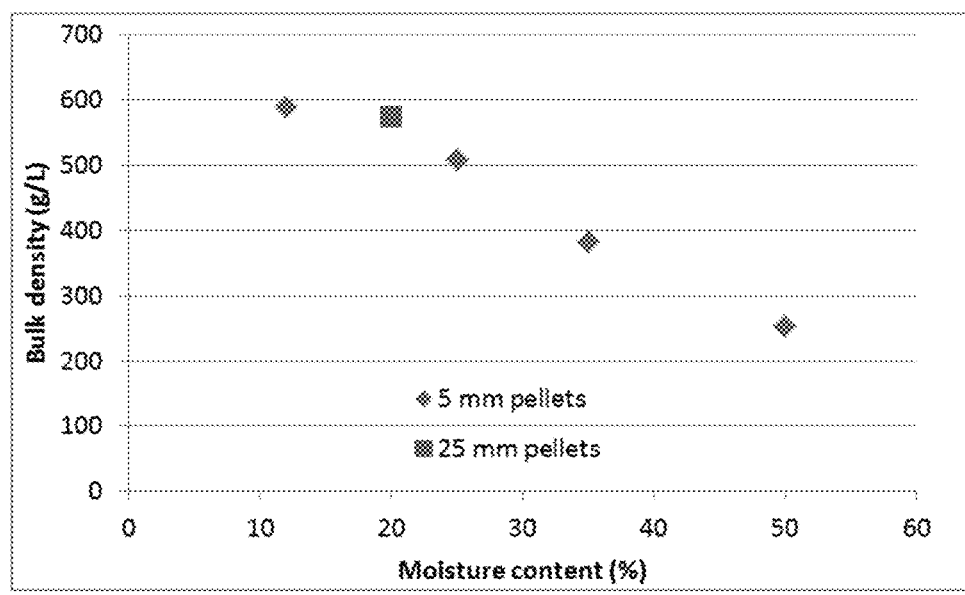
FIG. 8 is a graph showing bulk density for AFEX™-treated corn stover pellets produced at multiple sizes and moisture contents according to various embodiments.

Tetracycline and cycloheximide were added at final concentrations of 20 mg/L and 15 mg/L, respectively, to control fungal contamination. A citrate buffer was used to control pH as described in Example 8. Novozymes CTec2 and HTec2 enzyme were added at a protein loading of 7 mg and 3 mg per g pellet, respectively. After enzyme addition, the flasks were sealed and placed in a shake flask incubator set at 50° C. and 200 rpm rotation. A 1 mL sample was obtained at 1, 6, 24, 48, and 72 hours after enzyme was added and analyzed for sugar content as described in Example 9. The results are shown in FIG. 8. (Note that the line for 50% moisture is shifted 0.5 hours to the left for clarity.

As FIG. 8 shows, a glucose concentration above 60 g/L was obtained for all AFEX™-treated corn stover pellets within 48 hours. This concentration is sufficient for effective fermentation to ethanol or other value added products. The pellets also hydrolyze at a rapid rate, producing over 50% of the total sugars within the first 6 hours. Pellets produced at a higher moisture content tended to have greater sugar yields than pellets produced at low moisture content. However, the pellets produced at 50% moisture did not appreciably release more glucose than pellets produced at 35% moisture.

As demonstrated, AFEX™-treated biomass can be pelletized over a wide range of moisture contents and still be viable as a feedstock for fermentable sugar production. Depending on the economics and desires of the customers it may be possible to customize moisture content to provide a suitable combination of storability versus sugar concentration for any number of applications.

EXAMPLE 11

Prophetic

Samples of biomass, such as switchgrass and prairie cord grass will be collected at various maturities, and corn stover will be collected following grain harvest. Biomass composition will be determined at harvest, during storage in round bales, after initial AFEX™ processing and densification, and after storage of densified pellets. AFEX™ pretreatment will be statistically optimized for hydrolysis and binding properties based on parameters of time, temperature, biomass moisture, and ammonia to biomass ratio. AFEX™ conditions providing at least 90% of glucan conversion and 80% xylan conversion will be used to prepare materials for densification.

Densification will be performed using any suitable method, including the methods used in Examples 2, 3, or 8.

The resulting pellets will be subjected to various environmental conditions to simulate long-term storage, and then evaluated for flowability, compression strength, etc. Downstream processing characteristics will be evaluated using a standardized set of hydrolysis and fermentation conditions, including separate hydrolysis and fermentation (SHF) vs. simultaneous saccharification and fermentation (SSF). In one embodiment a comparison of these properties will be made between freshly prepared pellets (i.e., within about one (1) month), stored pellets and non-densified biomass.

EXAMPLE 12

Prophetic

AFEX™ pretreatment of prairie cord grass will be statistically optimized for time, temperature, biomass moisture, and ammonia to biomass ratio. A fairly broad range of AFEX™ pretreatment conditions gives similar hydrolysis results, giving us confidence that there are sets of pretreatment conditions that also enhance binding properties. AFEX™ pretreatment conditions providing at least 90% of glucan conversion and 80% xylan conversion will be identified and used to prepare materials for densification. We will characterize these pretreated materials for surface properties using various methods developed in our lab (ESCA, Prussian blue staining, SEM), and will correlate those properties with the pellet density and durability.

EXAMPLE 13

Prophetic

Operating variables will be investigated to optimize operating conditions for converting pretreated biomass into densified pellets. These variables include AFEX™ pretreatment conditions, moisture content, particle size, die temperature versus bond strength, rate of compaction versus quality of output, energy usage, existing surface chemistry and variations, compaction ratios and resultant density, and compacted package size and shape. Attrition and wear of mechanical components will also be assessed.

EXAMPLE 14

Prophetic

Biomass pretreated using any known AFEX™ procedure or according to the procedure in Example 1 or with any other appropriate modification of an AFEX™ procedure will be densified using any suitable method, including the methods described in Examples 2 and 3.

The densified biomass will then be subjected to various environmental conditions, including temperature (25 to 40° C.), relative humidity (60 to 90%), consolidation stress (0 to 120 kPa), and storage time (0 to 6 mo). Following storage, physical characteristics will be evaluated as described below:

Flowability may be evaluated with a simple test in which a number of AFEX™-pellets are placed in a container, such as the bed of a truck and tipped to about 45 degrees. A comparison with conventional pellets may be made by noting the time it takes for the pellets to flow out of the container.

Flowability will also be evaluated using Carr Indices. See ASTM D6393. 1999, *Standard test method for bulk solids characterization by Carr indices, ASTM Standards*, W. Conshohocken. Pa. Flowability is comprehensively defined as the ability of a material to flow un-abruptly under a given environmental condition. The flowability measurement is most often done by Carr Indices, by calculating the total flowability index and total floodability index. Carr, R. L. Jr. 1965, *Evaluating flow properties of solids, Chemical Engineering* 72(3): 163-168.

A higher value to total flowability index and lower value to total floodability index will yield an ideal material with low or no flow problems. Another way to quantify flowability is by measuring the Jenike Shear Stress properties. See Jenike, A. W. 1964, *Storage and flow of Bulletin No. 123*, Utah Engineering station, Bulletin of University of Utah. Jenike's method will also be used to determine particle cohesion, yield locus, angle of internal friction, yield strength, and flow function, and particle size distribution. See ASTM D6128. 2000, *Standard Test Method for Shear Testing of Bulk Solids Using the Jenike Shear Cell, ASTM Standards*, W. Conshohocken. Pa., and ASAE S19.3. 2003, *Method of determining and expressing fineness of feed materials by sieving, ASAE Standards*. St Joseph, Mich.: ASABE.

Additionally, glucan, xylan, galactan, arabinan, mannan, lignin, ash and fiber levels will be evaluated to determine their effect on storage and flowability behavior. Furthermore, several other physical properties will be measured as indicators of poor flowability (i.e., particle size, particle shape, thermal properties, moisture properties, and color). See Selig, M, et al., 2008, *Enzymatic saccharification of lignocellulosic biomass, Technical report NREL/TP-510-42629*; Sluiter, A, B. Hames, R. Ruiz, C. Scarlata, J. Sluiter, and D. Templeton, 2008a, *Determination of ash in biomass, Technical report NREL/TP-510-42622*; Sluiter, A, B. Hames, R. Ruiz, C. Scarlata, J. Sluiter, D. Templeton, and D. Crocker. 2008b, *Determination of structural carbohydrates and lignin in biomass, Technical report NREL/TP-510-42618*.

Rheological material properties that affect the ability of biomass to be handled pre- and post-densification will be established. Such properties include, but are not limited to, bulk density, true density, compressibility, relaxation, springback, permeability, unconfined yield strength, and frictional qualities. These properties are a function of the feedstock particle size and distribution, shape factor, moisture condition, and consolidation pressure and time. Since commercial rheological testers are typically designed for use with small grains and fine powders; and consequently, do not accommodate particulate that is greater than ¼ inch in diameter, we will develop new measurement systems for characterizing larger feedstock particles. Systems include compaction and shear cells that can be scaled for various material sizes, integrated with commercial load frames, and operated over a range of consolidation pressures.

Data will be analyzed to determine conditions which lead to improved (or optimized) flowability, using formal statistical methods such as general linear models, regression, response surface analysis, multivariate analysis, and other techniques as appropriate. See Myers, H. R. 1986, *Classical and modern regression applications*, $2^{nd}$ edition. Duxbury publications, CA. USA. Draper, N. R., and Smith, H. 1998, *Applied Regression Analysis*, New York, N.Y.: John Wiley and Sons, Inc.

EXAMPLE 15

Prophetic

At least three types of biomass will be evaluated, namely corn stover, switchgrass, and prairie cord grass. For each of these feedstocks, samples of raw ground biomass, AFEX™-pretreated biomass, and AFEX™-pretreated and densified biomass (before and after storage) will be collected. Thus, 3×4=12 total biomass sample types will be evaluated. Separate hydrolysis and fermentation (SHF) will be evaluated. For saccharification, flasks will be incubated for 48 h at 50° C. and 250 rpm in an orbital shaker. Samples will be removed at 0, 2, 4, 6, 8, 18, 24, 30, 36, and 48 hr. Flasks will then be cooled to 30° C. and inoculated with 2 ml of a 12-18 h culture of a recombinant strain of *Saccharomyces cerevisiae* which possesses pentose-fermenting capabilities grown in a medium containing two (2) g/l glucose and two (2) g/l yeast extract. Flasks will be incubated for an additional 96 h at 30° C. and 150 rpm in an orbital shaker. Samples will be removed at 0, 3, 6, 9, 18, 24, 36, 48, 60, 72, 84, and 96 hr during fermentation.

Simultaneous saccharification and fermentation (SSF) will also be performed to evaluate conversion. The main difference will be that flasks will be dosed with enzyme and immediately inoculated with yeast as noted above, then incubated for 144 hr at 30° C. Samples will be removed at 0, 2, 4, 6, 8, 18, 24, 36, 48, 60, 72, 96, 120, and 144 hr. Enzyme and biomass loadings and other conditions will be identical to those listed above.

Novel densified biomass products and methods for making and using same are described herein. In one embodiment, a conventional pretreatment is used to produce a tacky biomass which, surprisingly, is easily convertible to a solid hydrolysable particulate without the use of added binder. The hydrolysable particulates are also surprisingly at least as dense and demonstrate superior hardness properties as compared with conventional densified particulates produced with and/or containing added binder(s).

In one embodiment, hydrolysable particulates comprising more than one type of biomass material (e.g., corn stover, grasses, and/or wood, and the like) are provided. In this way, a commodity hydrolysable solid biomass product having relatively uniform properties is provided which may be more easily adopted into the biomass processing industry. Such properties may include, but are not limited to, BTU content, sugar content, and so forth.

Any suitable type of densification process may be used to produce products having a variety of sizes and shapes. In one embodiment, the densification process device uses a gear mesh system to compress biomass through a tapering channel between adjacent gear teeth, forming high density hydrolysable particulates. In one embodiment, the system operates at lower temperature, pressure, and energy requirements than conventional processes.

In one embodiment, the pretreated hydrolysable particulates "hold up" better, i.e., are more resistant to physical forces, during shipping, handling and/or storing as compared to particulates which are not pretreated. In one embodiment, the resulting products have an increased flowability as compared with conventional biomass solids, which allow for automated loading and unloading of transport vehicles and storage systems, as well as transport through the processing facility.

All publications, patents and patent documents are incorporated by reference herein, as though individually incorporated by reference, each in their entirety, as though individually incorporated by reference. In the case of any inconsistencies, the present disclosure, including any definitions therein, will prevail.

Although specific embodiments have been illustrated and described herein, it will be appreciated by those of ordinary skill in the art that any procedure that is calculated to achieve the same purpose may be substituted for the specific embodiments shown. For example, although the process has been discussed using particular types of plant biomass, any type of plant biomass or other types of biomass or biofuels, such as agricultural biofuels, for example, may be used. This application is intended to cover any adaptations or variations of the present subject matter. Therefore, it is manifestly intended that embodiments of this invention be limited only by the claims and the equivalents thereof.

What is claimed is:

1. A method comprising:
enzymatically hydrolyzing one or more hydrolysable densified biomass particulates to produce a convertible sugar-containing stream, wherein said densified biomass particulates are produced by:
subjecting a quantity of plant biomass fibers containing lignin and/or hemicellulose to a pretreatment to cause at least a portion of the lignin and/or hemicellulose in said biomass fibers to move to an outer surface to produce a quantity of pretreated tacky plant biomass fibers; and
densifying said pretreated tacky plant biomass fibers to produce the one or more hydrolysable densified biomass particulates, wherein said densified plant biomass fibers are densified without using added binder.

2. The method of claim 1 wherein the solids loading is about 12% to about 35%, or from about 12% to about 20%, or from about 18% to about 24%.

3. The method of claim 1 wherein said biomass fibers are corn stover fibers, switchgrass fibers, wood fibers, prairie cord grass fibers, or combinations thereof.

4. The method of claim 1 wherein the pretreatment and the densifying steps are performed as an integrated process at a single location.

5. The method of claim 1 wherein the pretreatment is an ammonia pretreatment or a sodium hydroxide pretreatment.

6. The method of claim 5 wherein the ammonia pretreatment is liquid ammonia fiber expansion (AFEX) pretreatment or a gaseous AFEX pretreatment.

7. The method of claim 5 wherein the method further comprises adding water and/or steam to said biomass fibers prior to and/or during the pretreatment.

8. The method of claim 1 wherein the convertible sugar-containing stream is fermented to produce a bioproduct.

9. The method of claim 8 wherein the bioproduct is a biofuel.

10. A product produced according to the method of claim 1.

11. A system comprising:
a hydrolyzing facility for enzymatically hydrolyzing one or more hydrolysable densified biomass particulates to produce a convertible sugar-containing stream, wherein said densified biomass particulates are produced by:
subjecting a quantity of plant biomass fibers containing lignin and/or hemicellulose to a pretreatment to cause at least a portion of the lignin and/or hemicellulose in said biomass fibers to move to an outer surface to produce a quantity of pretreated tacky plant biomass fibers; and
densifying said pretreated tacky plant biomass fibers to produce the one or more hydrolysable densified biomass particulates wherein said densified plant biomass fibers are densified without using added binder.

12. The system of claim 11 wherein the hydrolyzing facility is part of a bioproduct production facility, and the convertible sugar-containing stream is fermented in the bioproduct production facility to produce a bioproduct.

13. The system of claim 12 wherein the bioproduct production facility is an ethanol production facility and/or said biomass fibers are corn stover fibers.

14. The system of claim 11 further comprising:
a pretreatment facility for the subjecting step; and
a densifying facility for the densifying step.

15. The system of claim 11 wherein the pretreatment is an ammonia pretreatment or a sodium hydroxide pretreatment.

16. The system of claim 15 wherein the ammonia pretreatment is liquid ammonia fiber expansion (AFEX) pretreatment or a gaseous AFEX pretreatment.

17. The system of claim 14 wherein the pretreatment facility and densifying facility are co-located.

18. The method of claim 1 wherein sugar in the convertible sugar-containing stream is produced from said densified biomass particulates at a faster rate as compared to a sugar-containing stream produced using non-densified biomass.

19. The product of claim 10 wherein the fermentable sugar-containing stream contains glucose, xylose, mannose, arabinose, or a combination thereof.

20. A method comprising:
subjecting a quantity of plant biomass fibers containing lignin and/or hemicellulose to a pretreatment to cause at least a portion of the lignin and/or hemicellulose in said biomass to move to an outer surface to produce a quantity of pretreated tacky plant biomass fibers;
densifying said pretreated tacky plant biomass fibers to produce the one or more hydrolysable densified biomass particulates wherein said biomass fibers is densified without using added binder; and
enzymatically hydrolyzing the one or more hydrolysable densified biomass particulates to produce a convertible sugar-containing stream, wherein, the subjecting, densifying and enzymatically hydrolyzing steps are performed as an integrated process at a single location.

21. A method comprising:
providing a hydrolysable densified biomass particulate or a plurality thereof, the hydrolysable densified biomass particulate or particulates each comprising a plurality of plant biomass fibers containing lignin and/or hemicellulose at an outer surface of the fibers, wherein the hydrolysable densified biomass particulate or particulates are in a compressed particulate form and are free from added binder; and
hydrolyzing the hydrolysable densified biomass particulate or plurality thereof to produce a convertible sugar-containing stream.

22. The method of claim 1 wherein the hydrolyzing is performed in a tank having an impeller located therein, wherein an impeller to tank diameter ratio is from 1:4 to 3:4.

23. The method of claim 6 wherein the ammonia pretreatment is performed in a pretreatment vessel and the method further comprises removing residual ammonia remaining after the subjecting step by introducing steam into the pretreatment vessel.

24. The system of claim 11 wherein the hydrolyzing is performed in a tank having an impeller located therein, wherein an impeller to tank diameter ratio is from 1:4 to 3:4.

25. The system of claim 14 wherein the pretreatment facility includes an apparatus for adding steam and/or water to the plant biomass fibers prior to and/or during the pretreatment.

26. The system of claim 16 wherein the ammonia pretreatment is performed in a pretreatment vessel and residual ammonia is removed after the subjecting step by introducing steam into the pretreatment vessel.

27. The method of claim 1 wherein the subjecting step takes place in a stirred reactor.

28. The method of claim 27 wherein the stirred reactor is a vertical stirred reactor.

29. The system of claim 11 wherein the subjecting step takes place in a stirred reactor.

30. The system of claim 29 wherein the stirred reactor is a vertical stirred reactor.

* * * * *

UNITED STATES PATENT AND TRADEMARK OFFICE
CERTIFICATE OF CORRECTION

PATENT NO. : 9,458,482 B2
APPLICATION NO. : 14/579377
DATED : October 4, 2016
INVENTOR(S) : Bryan Bals et al.

It is certified that error appears in the above-identified patent and that said Letters Patent is hereby corrected as shown below:

On the Title Page

Item [56]

Page 3/Other Publications/Column 1/Line 27: "reads as "Zymornanas" and should read as "Zymomonas"
Page 3/Other Publications/Column 1/Lines 38-39: reads as "of Pretreated Pretreated Corn'" and should read as "of Pretreated Corn"
Page 3/Other Publications/Column 1/Line 49: reads as "Performace" and should read as "Performance"
Page 3/Other Publications/Column 2/Line 4: reads as "846-889." and should read as "848-889."
Page 3/Other Publications/Column 2/Line 5: reads as "Mosler" and should read as "Mosier"
Page 3/Other Publications/Column 2/Line 6: reads as "Lignocellulosio" and should read as "Lignocellulosic"
Page 3/Other Publications/Column 2/Line 6: reads as "at" and should read as "et"
Page 4/Other Publications/Column 1/Line 10: reads as "Feedstuff'," and should read as "Feedstuffs","
Page 4/Other Publications/Column 1/Line 60: reads as "dated" and should read as "mailed"
Page 4/Other Publications/Column 2/Line 50: reads as "Feasibiiity" and should read as "Feasibility"
Page 5/Other Publications/Column 1/Line 4: reads as "2002," and should read as "2005,"
Page 5/Other Publications/Column 1/Line 45: reads as "Ammonia-Recyced Percolation Process or Pretreament" and should read as "Ammonia-Recycled Percolation Process for Pretreatment"
Page 5/Other Publications/Column 1/Line 46: reads as "Feedsock" and should read as "Feedstock"
Page 5/Other Publications/Column 1/Line 66: reads as "Communicaton pusuant" and should read as "Communication pursuant"
Page 5/Other Publications/Column 2/Line 1: reads as "or" and should read as "for"
Page 5/Other Publications/Column 2/Line 32: reads as "11650707.8," and should read as "11850707.8,"
Page 5/Other Publications/Column 2/Line 57: reads as "mated" and should read as "mailed"
Page 6/Other Publications/Column 2/Line 11: reads as "pages." and should read as "pages (Official Copy Only)."

Signed and Sealed this
Fifth Day of December, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,458,482 B2

Page 6/Other Publications/Column 2/Line 13: reads as "pages." and should read as "pages (English Translation Only)."
Page 6/Other Publications/Column 2/Line 14: reads as "Braziiian" and should read as "Brazilian"
Page 6/Other Publications/Column 2/Line 21: reads as "pages)." and should read as "pages of Official Copy)."
Page 6/Other Publications/Column 2/Line 24: reads as "pages)." and should read as "pages of Official Copy)."
Page 6/Other Publications/Column 2/Line 27: reads as "pages)." and should read as "pages of Official Copy)."
Page 6/Other Publications/Column 2/Line 30: reads as "pages)." and should read as "pages of Official Copy)."
Page 6/Other Publications/Column 2/Line 33: reads as "pages)." and should read as "pages of Official Copy)."

In the Specification

Column 5/Line 53: reads as "pre treatments," and should read as "pretreatments,"
Column 10/Line 1: reads as "(AFEX™)" and should read as "(AFEX™),"
Column 13/Lines 1-2: reads as "cellobiohydralases," and should read as "cellobiohydrolases,"
Column 16/Line 6: reads as "The condensation gaseous AFEX™ process pretreatment" and should read as "The gaseous AFEX™ pretreatment"
Column 17/Lines 4-5: reads as "82.1+g" and should read as "82.1g"
Column 19/Line 9: reads as "Repose)(°" and should read as "Repose(°)"
Column 19/Line 57: "reads as "Sumnu" and should read as "Sumnu,"
Column 23/Line 16: reads as "Ga.)." and should read as "Ga.)"
Column 27/Line 6: reads as "samples." and should read as "samples"
Column 27/Lines 55-56: reads as "(Parsipanny," and should read as "(Parsippany,"
Column 29/Line 12: reads as "AFEX®-treated corn stover" and should read as "AFEX™-treated corn stover,"

In the Claims

Column 37 Line 38 Claim 7: reads as "said biomass" and should read as "said plant biomass"